(12) United States Patent
Firminger et al.

(10) Patent No.: US 8,010,664 B2
(45) Date of Patent: Aug. 30, 2011

(54) HYPOTHESIS DEVELOPMENT BASED ON SELECTIVE REPORTED EVENTS

(75) Inventors: Shawn P. Firminger, Redmond, WA (US); Jason Garms, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 203 days.

(21) Appl. No.: 12/455,309

(22) Filed: May 28, 2009

(65) Prior Publication Data
US 2010/0131449 A1 May 27, 2010

Related U.S. Application Data

(63) Continuation-in-part of application No. 12/313,659, filed on Nov. 21, 2008, and a continuation-in-part of application No. 12/315,083, filed on Nov. 26, 2008, and a continuation-in-part of application No. 12/319,135, filed on Dec. 31, 2008, now Pat. No. 7,937,465, and a continuation-in-part of application No. 12/319,134, filed on Dec. 31, 2008, now Pat. No. 7,945,632, and a continuation-in-part of application No. 12/378,162, filed on Feb. 9, 2009, and a continuation-in-part of application No. 12/378,288, filed on Feb. 11, 2009, and a continuation-in-part of application No. 12/380,409, filed on Feb. 25, 2009, and a continuation-in-part of application No. 12/380,573, filed on Feb. 26, 2009, and a continuation-in-part of application No. 12/383,581, filed on Mar. 24, 2009, and a continuation-in-part of application No. 12/383,817, filed on Mar. 25, 2009, and a continuation-in-part of application No. 12/384,660, filed on Apr. 6, 2009, and a continuation-in-part of application No. 12/384,779, filed on Apr. 7, 2009, and a continuation-in-part of application No. 12/387,487, filed on Apr. 30, 2009, and a continuation-in-part of application No. 12/387,465, filed on Apr. 30, 2009.

(51) Int. Cl.
*G06F 15/16* (2006.01)
*G06F 17/30* (2006.01)

(52) U.S. Cl. ........ 709/224; 709/204; 709/206; 709/217; 707/687; 707/755; 707/736; 706/11; 706/12; 706/52; 705/2

(58) Field of Classification Search ................. 709/224, 709/217
See application file for complete search history.

(56) References Cited

U.S. PATENT DOCUMENTS
3,599,149 A    8/1971   Pardoe
(Continued)

FOREIGN PATENT DOCUMENTS
WO    WO 99/18842    4/1999

OTHER PUBLICATIONS
U.S. Appl. No. 12/462,201, Firminger et al.
(Continued)

Primary Examiner — Jude Jean Gilles

(57) ABSTRACT

A computationally implemented method includes, but is not limited to: acquiring events data including data indicating incidence of a first one or more reported events and data indicating incidence of a second one or more reported events, at least one of the first one or more reported events and the second one or more reported events being associated with a user; determining an events pattern based selectively on the incidences of the first one or more reported events and the second one or more reported events; and developing a hypothesis associated with the user based, at least in part, on the determined events pattern. In addition to the foregoing, other method aspects are described in the claims, drawings, and text forming a part of the present disclosure.

64 Claims, 21 Drawing Sheets

U.S. PATENT DOCUMENTS

| | | | |
|---|---|---|---|
| 7,203,430 B2 | 4/2007 | Ohta | |
| 7,400,928 B2 | 7/2008 | Hatlestsad | |
| 7,627,544 B2* | 12/2009 | Chkodrov et al. | 706/48 |
| 2003/0166277 A1 | 9/2003 | Zauderer et al. | |
| 2004/0103108 A1 | 5/2004 | Andreev et al. | |
| 2005/0102578 A1 | 5/2005 | Bliss et al. | |
| 2006/0034430 A1 | 2/2006 | Liakis | |
| 2007/0293731 A1 | 12/2007 | Downs et al. | |
| 2008/0034056 A1 | 2/2008 | Renger et al. | |
| 2008/0091515 A1 | 4/2008 | Thieberger et al. | |
| 2008/0215607 A1 | 9/2008 | Kaushansky et al. | |
| 2008/0218472 A1 | 9/2008 | Breen et al. | |
| 2009/0049154 A1* | 2/2009 | Ge | 709/217 |
| 2009/0077658 A1 | 3/2009 | King et al. | |
| 2009/0132197 A1 | 5/2009 | Rubin et al. | |
| 2009/0240647 A1 | 9/2009 | Green et al. | |
| 2009/0276221 A1 | 11/2009 | Heiman et al. | |
| 2009/0326981 A1 | 12/2009 | Karkanias et al. | |
| 2010/0010866 A1 | 1/2010 | Bal et al. | |
| 2010/0088104 A1 | 4/2010 | DeRemer et al. | |

OTHER PUBLICATIONS

U.S. Appl. No. 12/462,128, Firminger et al.
U.S. Appl. No. 12/459,854, Firminger et al.
U.S. Appl. No. 12/459,775, Firminger et al.
U.S. Appl. No. 12/456,433, Firminger et al.
U.S. Appl. No. 12/456,249, Firminger et al.
U.S. Appl. No. 12/455,317, Firminger et al.
U.S. Appl. No. 12/387,487, Firminger et al.
U.S. Appl. No. 12/387,465, Firminger et al.
U.S. Appl. No. 12/384,779, Firminger et al.
U.S. Appl. No. 12/384,660, Firminger et al.
U.S. Appl. No. 12/383,817, Firminger et al.
U.S. Appl. No. 12/383,581, Firminger et al.
U.S. Appl. No. 12/380,573, Firminger et al.
U.S. Appl. No. 12/380,409, Firminger et al.
U.S. Appl. No. 12/378,288, Firminger et al.
U.S. Appl. No. 12/378,162, Firminger et al.
U.S. Appl. No. 12/319,135, Firminger et al.
U.S. Appl. No. 12/319,134, Firminger et al.
U.S. Appl. No. 12/315,083, Firminger et al.
U.S. Appl. No. 12/313,659, Firminger et al.
Buchanan, Matt; "Twitter Toilet Tweets Your Poo"; gizmodo.com; bearing a date of May 18, 2009; pp. 1-2; located at http://gizmodo.com/5259381/twitter-toilet-tweets-your-poo; printed on Jul. 1, 2009.
Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered- as-the...; printed on Nov. 25, 2009.
Fox, Stuart; "The John, 2.0"; Popular Science; bearing a date of May 18, 2009; pp. 1-2; located at http://www.popsci.com/scitech/article/2009-05/john-20; printed on Jul. 1, 2009.
Frucci, Adam; "SNIF Dog Tags Track What Your Dog Does All Day; Spoiler: Eat, Sleep, Poop"; gizmodo.com; bearing a date of Jun. 10, 2009; pp. 1-2; located at http://i.gizmodo.com/5286076/snif-dog-tags-track-what-your-dog-does-all-day-spoiler-eat-sl...; printed on Jul. 1, 2009.
Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919...; printed on Nov. 25, 2009.

"hacklab.Toilet—a twitter-enabled toilet at hacklab.to"; aculei.net; bearing a date of May 18, 2009; pp. 1-8; located at http://aculei.net/~shardy/hacklabtoilet/; printed on Jul. 1, 2009.
June, Laura; "Apple patent filing shows off activity monitor for skiers, bikers"; engadget.com; bearing a date of Jun. 11, 2009; pp. 1-8; located at http://www.engadget.com/2009/06/11/apple-patent-filing-shows-off-a...; printed on Jul. 1, 2009.
Kraft, Caleb; "Twittering toilet"; Hack a Day; bearing a date of May 5, 2009; pp. 1-11; located at http://hackaday.com/2009/05/05/twittering-toilet/; printed on Jul. 1, 2009.
"Mobile pollution sensors deployed"; BBC News; bearing a date of Jun. 30, 2009; pp. 1-2; located at http://news.bbc.co.uk/2/hi/science/nature/8126498.stm; printed on Jul. 1, 2009; © BBC MMIX.
Oliver, Sam; "Apple developing activity monitor for skiers, snowboarders, bikers"; AppleInsider; bearing a date of Jun. 11, 2009; pp. 1-6; located at http://www.appleinsider.com/articles/09/06/11/apple_developing_act...; printed on Jul. 1, 2009; AppleInsider © 1997-2008.
Rettner, Rachael; "Cell Phones Allow Everyone to Be a Scientist"; LiveScience; bearing a date of Jun. 4, 2009; pp. 1-3; located at http://www.livescience.com/technology/090604-mobile-sensor.html; printed on Jul. 1, 2009; © Imaginova Corp.
Agger, Michael; "Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.
"Self-tracking links to get you started"; The Quantified Self: self knowledge through numbers; printed on Dec. 10, 2010; pp. 1-5; located at: http://quantifiedself.com/self-tracking-links-to-get-you-started/.
"Find Patterns in Data that Identify Combinations of Events that Occur Together"; SPSS Association Rule Components; Bearing a date of 2002; 5 Total Pages; SPSS Inc.; located at: http://www.spss.com/spssetd/files/AssocRuleTech.pdf.
"Find Sequential Patterns in Data to Predict Events More Accurately"; SPSS Sequence Association™ Component; Bearing a date of 2002; pp. 1-5; SPSS Inc.; located at: http://www.spss.com/spssetd/files/sequencetech.pdf.
Hansen, et al.; "Microblogging—Facilitating Tacit Knowledge?"—A Second Year Term Paper; Information Management Study at Copenhagen Business School; Bearing a date of 2008; pp. 1-42; located at http://www.scribd.com/doc/3460679/Microblogging-as-a-Facilitator-for-Tacit-Knowledge.
Morales, et al.; "Using Sequential Pattern Mining for Links Recommendation in Adaptive Hypermedia Educational Systems"; Current Developments in Technology-Assisted Education; Bearing a date of 2006; pp. 1016-1020; FORMATEX 2006; located at: http://www.formatex.org/micte2006/pdf/1016-1020.pdf.
Nesbit, et al.; "Sequential Pattern Analysis Software for Educational Event Data"; pp. 1-5; Simon Fraser University, Burnaby, Canada; located at: http://www.sfu.ca/~mzhou2/temp/MB2008_1.pdf.
Reiss, M.; "Correlations Between Changes in Mental States and Thyroid Activity After Different Forms of Treatment"; The British Journal of Psychology—Journal of Mental Science; Bearing dates of Mar. 6, 1954 and 1954; pp. 687-703 [Abstract only provided]; located at http://bjp.repsych.org/cgi/content/abstract/100/420/687; The Royal College of Psychiatrists.

* cited by examiner

HYPOTHESIS DEVELOPMENT BASED ON SELECTIVE REPORTED EVENTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

Related Applications

For purposes of the USPTO extra-statutory requirements, the present application constitutes a continuation-in-part of U.S. patent application Ser. No. 12/313,659, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 21 Nov. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/315,083, entitled CORRELATING SUBJECTIVE USER STATES WITH OBJECTIVE OCCURRENCES ASSOCIATED WITH A USER, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 26 Nov. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,135, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008 now U.S. Pat. No. 7,937,465, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/319,134, entitled CORRELATING DATA INDICATING AT LEAST ONE SUBJECTIVE USER STATE WITH DATA INDICATING AT LEAST ONE OBJECTIVE OCCURRENCE ASSOCIATED WITH A USER, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 31 Dec. 2008 now U.S. Pat. No. 7,945,632, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/378,162, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 9 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/378,288, entitled SOLICITING DATA INDICATING AT LEAST ONE OBJECTIVE OCCURRENCE IN RESPONSE TO ACQUISITION OF DATA INDICATING AT LEAST ONE SUBJECTIVE USER STATE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 11 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,409, entitled SOLICITING DATA INDICATING AT LEAST ONE SUBJECTIVE USER STATE IN RESPONSE TO ACQUISITION OF DATA INDICATING AT LEAST ONE OBJECTIVE OCCURRENCE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 25 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,573, entitled SOLICITING DATA INDICATING AT LEAST ONE SUBJECTIVE USER STATE IN RESPONSE TO ACQUISITION OF DATA INDICATING AT LEAST ONE OBJECTIVE OCCURRENCE, naming Shawn P. Firminger; Jason Garms; Edward K. Y. Jung; Chris D. Karkanias; Eric C. Leuthardt; Royce A. Levien; Robert W. Lord; Mark A. Malamud; John D. Rinaldo, Jr.; Clarence T. Tegreene; Kristin M. Tolle; Lowell L. Wood, Jr. as inventors, filed 26 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,581, entitled CORRELATING DATA INDICATING SUBJECTIVE USER STATES ASSOCIATED WITH MULTIPLE USERS WITH DATA INDICATING OBJECTIVE OCCURRENCES, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 24 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/383,817, entitled CORRELATING DATA INDICATING SUBJECTIVE USER STATES ASSOCIATED WITH MULTIPLE USERS WITH DATA INDICATING OBJECTIVE OCCURRENCES, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 25 Mar. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,660, entitled HYPOTHESIS BASED SOLICITATION OF DATA INDICATING AT LEAST ONE SUBJECTIVE USER STATE, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 6 Apr. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/384,779, entitled HYPOTHESIS BASED SOLICITATION OF DATA INDICATING AT LEAST ONE SUBJECTIVE USER STATE, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 7 Apr. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,487, entitled HYPOTHESIS BASED SOLICITATION OF DATA INDICATING AT LEAST ONE OBJECTIVE OCCURRENCE, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 30 Apr. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/387,465, entitled HYPOTHESIS BASED SOLICITATION OF DATA INDICATING AT LEAST ONE OBJECTIVE OCCURRENCE, naming Shawn P. Firminger, Jason Garms, Edward K. Y. Jung, Chris D. Karkanias, Eric C. Leuthardt, Royce A. Levien, Robert W. Lord, Mark A. Malamud, John D. Rinaldo, Jr., Clarence T. Tegreene, Kristin M. Tolle, and Lowell L. Wood, Jr., as inventors, filed 30 Apr. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

A computationally implemented method includes, but is not limited to acquiring events data including data indicating incidence of a first one or more reported events and data indicating incidence of a second one or more reported events, at least one of the first one or more reported events and the second one or more reported events being associated with a user; determining an events pattern based selectively on the incidences of the first one or more reported events and the second one or more reported events; and developing a hypothesis associated with the user based, at least in part, on the determined events pattern. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for acquiring events data including data indicating incidence of a first one or more reported events and data indicating incidence of a second one or more reported events, at least one of the first one or more reported events and the second one or more reported events being associated with a user; means for determining an events pattern based selectively on the incidences of the first one or more reported events and the second one or more reported events; and means for developing a hypothesis associated with the user based, at least in part, on the determined events pattern. In addition to the foregoing, other system aspects are described in the claims, drawings, and text forming a part of the present disclosure.

A computationally implemented system includes, but is not limited to: circuitry for acquiring events data including data indicating incidence of a first one or more reported events and data indicating incidence of a second one or more reported events, at least one of the first one or more reported events and the second one or more reported events being associated with a user; circuitry for determining an events pattern based selectively on the incidences of the first one or more reported events and the second one or more reported events; and circuitry for developing a hypothesis associated with the user based, at least in part, on the determined events pattern. In addition to the foregoing, other system aspects are described in the claims, drawings, and text forming a part of the present disclosure.

A computer program product including a signal-bearing medium bearing one or more instructions acquiring events data including data indicating incidence of a first one or more reported events and data indicating incidence of a second one or more reported events, at least one of the first one or more reported events and the second one or more reported events being associated with a user; one or more instructions for determining an events pattern based selectively on the incidences of the first one or more reported events and the second one or more reported events; and one or more instructions for developing a hypothesis associated with the user based, at least in part, on the determined events pattern. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
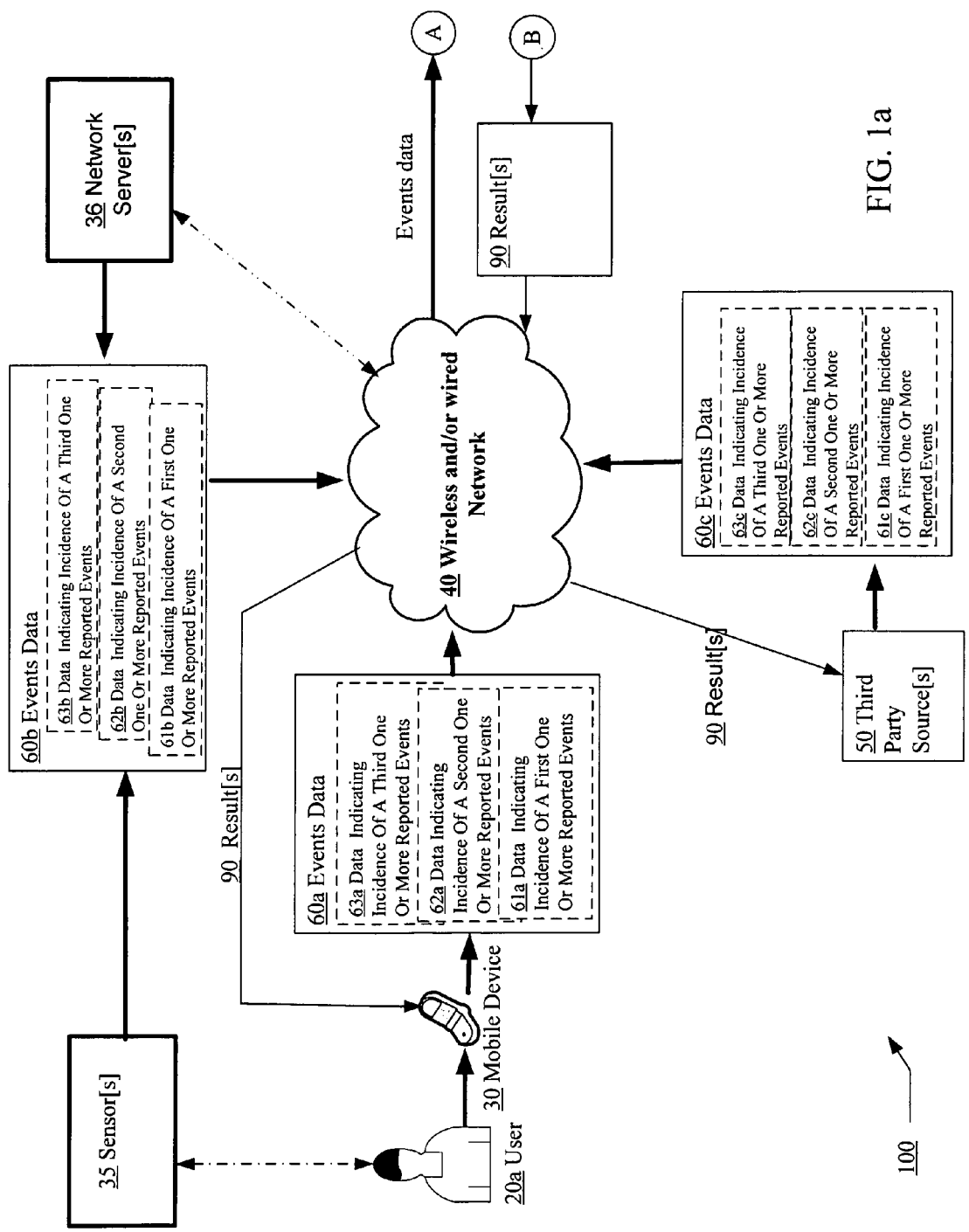
FIGS. 1a and 1b show a high-level block diagram of a mobile device 30 and a computing device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that is becoming increasingly popular in the computing/communication field is to electronically record one's feelings, thoughts, and other aspects of the person's everyday life onto an open diary. One place where such open diaries are maintained are at social networking sites commonly known as "blogs" where users may report or post their latest status, personal activities, and various other aspects of the users' everyday life. The process of reporting or posting blog entries is commonly referred to as blogging. Other social networking sites may allow users to update their personal information via, for example, social networking status reports in which a user may report or post for others to view their current status, activities, and/or other aspects of the user.

A more recent development in social networking is the introduction and explosive growth of microblogs in which individuals or users (referred to as "microbloggers") maintain open diaries at microblog websites (e.g., otherwise known as "twitters") by continuously or semi-continuously posting microblog entries. A microblog entry (e.g., "tweet") is typically a short text message that is usually not more than 140 characters long. The microblog entries posted by a microblogger may report on any aspect of the microblogger's daily life. Typically, such microblog entries will describe the various "events" associated with or are of interest to the microblogger that occurs during a course of a typical day. The microblog entries are often continuously posted during the course of a typical day, and thus, by the end of a normal day, a substantial number of events may have been reported and posted.

Each of the reported events that may be posted through microblog entries may be categorized into one of at least three possible categories. The first category of events that may be reported through microblog entries are "objective occurrences" that may or may not be associated with the microblogger. Objective occurrences that are associated with a microblogger may be any characteristic, incident, happening, or any other event that occurs with respect to the microblogger or are of interest to the microblogger that can be objectively reported by the microblogger, a third party, or by a device. Such events would include, for example, intake of food, medicine, or nutraceutical, certain physical characteristics of the microblogger such as blood sugar level or blood pressure that can be objectively measured, activities of the microblogger observable by others or by a device, activities of others that may or may not be of interest to the microblogger, external events such as performance of the stock market (which the microblogger may have an interest in), performance of a favorite sports team, and so forth. In some cases, objective occurrences may not be at least directly associated with a microblogger. Examples of such objective occurrences include, for example, external events that may not be directly related to the microblogger such as the local weather, activities of others (e.g., spouse or boss) that may directly or indirectly affect the microblogger, and so forth.

A second category of events that may be reported or posted through microblog entries include "subjective user states" of the microblogger. Subjective user states of a microblogger may include any subjective state or status associated with the microblogger that can only be typically reported by the microblogger (e.g., generally cannot be directly reported by a third party or by a device). Such states including, for example, the subjective mental state of the microblogger (e.g., happiness, sadness, anger, tension, state of alertness, state of mental fatigue, jealousy, envy, and so forth), the subjective physical state of the microblogger (e.g., upset stomach, state of vision, state of hearing, pain, and so forth), and the subjective overall state of the microblogger (e.g., "good," "bad," state of overall wellness, overall fatigue, and so forth). Note that the term "subjective overall state" as will be used herein refers to those subjective states that may not fit neatly into the other two categories of subjective user states described above (e.g., subjective mental states and subjective physical states).

A third category of events that may be reported or posted through microblog entries include "subjective observations" made by the microblogger. A subjective observation is any subjective opinion, thought, or evaluation relating to any incidence. Examples include, for example, a microblogger's perception about the subjective user state of another person (e.g., "he seems tired"), a microblogger's perception about another person's activities (e.g., "he drank too much yesterday"), a microblogger's perception about an external event (e.g., "it was a nice day today"), and so forth. Although microblogs are being used to provide a wealth of personal information, thus far they have been primarily limited to their use as a means for providing commentaries and for maintaining open diaries.

In accordance with various embodiments, methods, systems, and computer program products are provided to, among other things, develop one or more hypotheses that may be specific to a particular person (e.g. a microblogger) based on selective reported events. The methods, systems, and computer program products may be employed in a variety of environments including, for example, social networking environments, blogging or microblogging environments, instant messaging (IM) environments, or any other type of environment that allows a user to maintain a diary. A "hypothesis," as referred to herein, may define one or more relationships or links between a first one or more event types (e.g., a type of event such as a particular type of subjective user state, for example, "happy") and a second one or more event types (e.g., another type of event such as particular type of objective occurrence, for example, favorite sports team winning). In some embodiments, a hypothesis may, at least in part, be defined or represented by an events pattern that indicates or suggests a spatial or a sequential (e.g., time/temporal) relationship between different event types. Such a hypothesis, in some cases, may also indicate the strength or weakness of the link between the different event types. That is, the strength (e.g., soundness) or weakness of the correlation between different event types may depend upon, for example, whether the events pattern repeatedly occurs.

In various embodiments, the development of such a hypothesis may be particularly useful to the user that the hypothesis is associated with. That is, in some cases, the hypothesis may assist the user in modifying his/her future behavior, while in other cases; such a hypothesis may simply alert or notify the user that a pattern of events are repeatedly occurring. In other situations, such a hypothesis may be useful to third parties such as advertisers in order to assist the advertisers in developing a more targeted marketing scheme. In still other situations, such a hypothesis may help in the treatment of ailments associated with the user.

In the case where a hypothesis is being developed for a particular user, such as a microblogger, the methods, systems, and computer program products may be able to disregard or ignore reported events that may not be relevant to the development of the hypothesis. In particular, during a course of a typical day, a user such as microblogger may post a large volume of data that indicates numerous events that may have occurred during the course of the day. It is likely that a vast majority of these reported events may not be relevant to the development of a particular hypothesis. Thus, these methods, systems, and computer program products may distinguish between relevant and non-relevant data. In other words, to disregard or ignore those reported events that may not be relevant to the development of the hypothesis and use only selective reported events for developing the hypothesis. Note that the hypothesis to be developed may or may not determine a causal relationship between multiple events. Instead, the developed hypothesis may merely indicate that there is some sort of relationship (e.g., spatial or time/temporal sequential relationship) between multiple events.

As briefly described above, a hypothesis may be represented by an events pattern that may indicate spatial or sequential (e.g., time or temporal) relationship or relationships between multiple event types. In some implementations, a hypothesis may indicate temporal sequential relationships between multiple event types that merely indicate the temporal relationships between multiple event types. In alternative implementations a hypothesis may indicate a more specific time relationship between multiple event types. For example, a sequential pattern may represent the specific pattern of events that occurs along a timeline that may indicate the specific time intervals between event types.

Figure 1B:
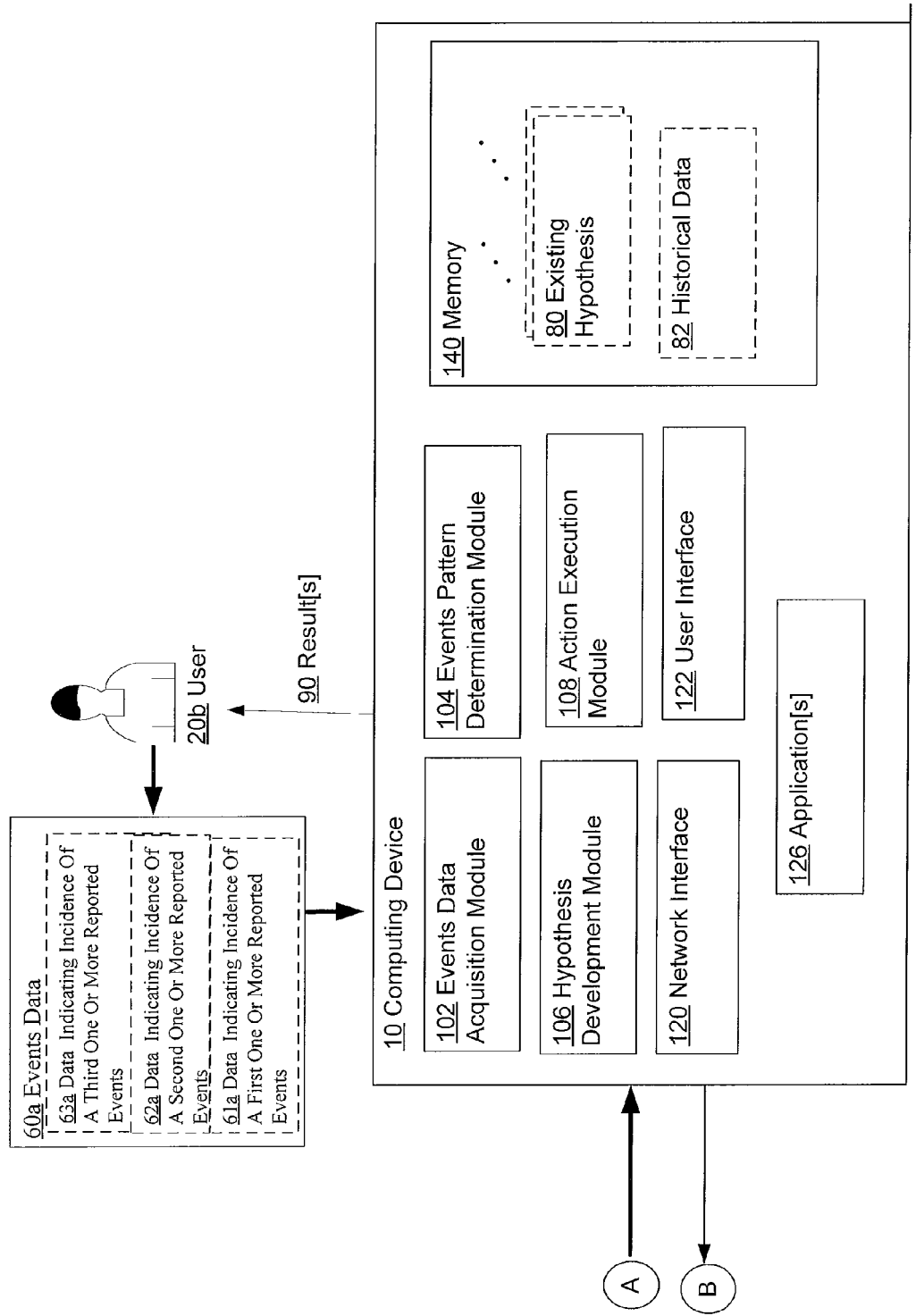

FIGS. 1a and 1b illustrate an example environment in accordance with various embodiments. In the illustrated environment, an exemplary system 100 may include at least a computing device 10 (see FIG. 1b). The computing device 10, which may be a server (e.g., network server) or a standalone device, may be employed in order to, among other things, acquire events data 60* including at least data indicating incidence of a first one or more reported events 61* and data indicating incidence of a second one or more reported events 62*, where at least one of the first one or more reported events and the second one or more reported events being associated with a user 20*. The computing device 10 may then be configured to determine an events pattern based selectively on the incidences of the first one or more reported events and the second one or more reported events. Based on the determined events pattern, the computing device 10 may then develop a hypothesis associated with the user 20*.

As indicated earlier, in some embodiments, the computing device 10 may be a server while in other embodiments, the computing device 10 may be a standalone device. In the case where the computing device 10 is a network server, the computing device 10 may communicate indirectly with a user 20a via wireless and/or wired network 40. In contrast, when the computing device 10 is a standalone device, it may communicate directly with a user 20b via a user interface 122 (see FIG. 1b). In the following, "*" indicates a wildcard. Thus, the reference to user 20* may indicate a user 20a or a user 20b of FIGS. 1a and 1b.

In embodiments in which the computing device 10 is a network server, the computing device 10 may communicate with a user 20a via a mobile device 30 and through a wireless and/or wired network 40. A network server, as will be described herein, may be in reference to a server located at a single network site or located across multiple network sites or a conglomeration of servers located at multiple network sites. The mobile device 30 may be a variety of computing/communication devices including, for example, a cellular phone, a personal digital assistant (PDA), a laptop, a desktop, or other types of computing/communication device that can communicate with the computing device 10. In some embodiments, the mobile device 30 may be a handheld device such as a cellular telephone, a smartphone, a Mobile Internet Device (MID), an Ultra Mobile Personal Computer (UMPC), a convergent device such as a personal digital assistant (PDA), and so forth.

In embodiments in which the computing device 10 is a standalone computing device 10 (or simply "standalone device") that communicates directly with a user 20b, the computing device 10 may be any type of mobile device 30 (e.g., a handheld device) or stationary device (e.g., desktop computer or workstation). For these embodiments, the computing device 10 may be a variety of computing/communication devices including, for example, a cellular phone, a personal digital assistant (PDA), a laptop, a desktop, or other types of computing/communication device. In some embodiments, in which the computing device 10 is a handheld device, the computing device 10 may be a cellular telephone, a smartphone, an MID, an UMPC, a convergent device such as a PDA, and so forth. In various embodiments, the computing device 10 may be a peer-to-peer network component device. In some embodiments, the computing device 10 and/or the mobile device 30 may operate via a Web 2.0 construct (e.g., Web 2.0 application 268).

In various embodiments, the computing device 10 may be configured to acquire events data 60* from one or more sources. Events data 60*, as will be described herein, may indicate the occurrences of multiple reported events. Each of the reported events may or may not be associated with a user 20*. In some embodiments, a reported event may be associated with the user 20* if it is reported by the user 20* or it is related to some aspect about the user 20* (e.g., the location of the user 20*, the local weather of the user 20*, activities performed by the user 20*, physical characteristics of the user 20* as detected by a sensor 35, subjective user state of the user 20*, and so forth). At least three different types of reported events may be indicated by the events data 60*, subjective user states associated with a user 20*, objective occurrences, and subjective observations made by the user 20* or by others (e.g., third party sources 50).

The events data 60*, in various embodiments and as illustrated in FIG. 1a, may include at least data indicating incidence of a first one or more reported events 61* and data indicating incidence of a second one or more reported events 62*. In some embodiments, the events data 60* may further include data indicating incidence of a third one or more reported events 63*. Although not depicted, additional reported events may be indicated by the events data 60* in various alternative embodiments.

As will be further described herein, in the following examples and illustrations, the first one or more reported events and the second one or more reported events may form the basis for developing a hypothesis. In contrast, the third one or more reported events may represent events that may not be relevant to the development of the hypothesis. In other words, the third one or more reported events may represent "noise" and may be ignored in the development of a hypothesis. That is, noise data must be accounted for particularly in, for example, the microblogging and social networking environments where much of the reported events posted through microblog entries and status reports may not be relevant to the development of a hypothesis. Such noise data may be filtered out prior to developing a useful hypothesis.

The events data 60* including the data indicating incidence of a first one or more reported events 61* and the data indicating incidence of a second one or more reported events 62* may be obtained from one or more distinct sources (e.g., the original sources for data). For example, in some implementations, a user 20* may provide at least a portion of the events data 60* (e.g., events data 60a that may include data indicating incidence of a first one or more reported events 61a, data indicating incidence of a second one or more reported events 62a, and/or data indicating incidence of a third one or more reported events 63a).

In the same or different embodiments, one or more remote network devices including one or more sensors 35 and/or one or more network servers 36 may provide at least a portion of the events data 60* (e.g., events data 60b that may include data indicating incidence of a first one or more reported events 61b, data indicating incidence of a second one or more reported events 62b, and/or data indicating incidence of a third one or more reported events 63b). In same or different embodiments, one or more third party sources may provide at least a portion of the events data 60* (e.g., events data 60c that may include data indicating incidence of a first one or more reported events 61c, data indicating incidence of a second one or more reported events 62c, and/or data indicating incidence of a third one or more reported events 63c). In still other embodiments, at least a portion of the events data 60* may be retrieved from a memory 140 in the form of historical data 82.

The one or more sensors 35 illustrated in FIG. 1a may represent a wide range of devices that can monitor various aspects or events associated with a user 20a (or user 20b). For example, in some implementations, the one or more sensors 35 may include devices that can monitor the user's physiological characteristics such as blood pressure sensors, heart rate monitors, glucometers, and so forth. In some implementations, the one or more sensors 35 may include devices that can monitor activities of a user 20* such as a pedometer, a toilet monitoring system (e.g., to monitor bowel movements), exercise machine sensors, and so forth. The one or more sensors 35 may also include other types of sensor/monitoring devices such as video or digital camera, global positioning system (GPS) to provide data that may be related to a user 20* (e.g., locations of the user 20*), and so forth.

The one or more third party sources 50 illustrated in FIG. 1a may represent a wide range of third parties and/or the network devices associated with such parties. Examples of third parties include, for example, health care entities (e.g., dental or medical clinic, hospital, physician's office, medical lab, and so forth), content providers, businesses such as retail business, other users (e.g., other microbloggers or other social networking site users), employers, athletic or social groups, educational entities such as colleges and universities, and so forth.

In brief, after acquiring the events data 60* from one or more sources, the computing device 10 may determine an events pattern based selectively (e.g., by disregarding the third one or more reported events or other noise data) on the incidences of the first one or more reported events and the second one or more reported events as indicated by the events data 60*. The events pattern may at least identify the link or relationship (e.g., spatial or sequential relationship) between the first one or more reported events and the second one or more reported events.

After determining the events pattern, the computing device 10 may be configured to develop a hypothesis associated with the user 20* based, at least in part, on the determined events pattern. The development of the hypothesis may involve creation of a new hypothesis in some cases while in other cases; it may involve the refinement of an already existing hypothesis 80. The creation of the hypothesis may be based, in addition to the events pattern, on historical data 82 that may be particularly associated with the user 20* or with a subgroup of the general population that the user 20* belongs to. In some embodiments, the historical data 82 may be historical medical data specific to the user 20* or to the subgroup of the general population, or may be events data 60* that indicate past reported events (that may or may not be associated with the user 20*). Other types of past data may also be included in the historical data 82 in various alternative embodiments.

After developing the hypothesis, in some implementations, the computing device 10 may be designed to execute one or more actions. One such action that may be executed is to present one or more results 90 of the hypothesis development operations. For example, the computing device 10 may present the results 90 to the user 20* (e.g., by transmitting the results to the user 20a or indicating the results 90 to the user 20b via a user interface 122), to one or more third parties (e.g., one or more third party sources 50), and/or to one or more remote network devices (e.g., network servers 36). The results 90 to be presented may include the developed hypothesis, an advisory based on the hypothesis, a recommendation based on the hypothesis, or other types of results.

As illustrated in FIG. 1b, computing device 10 may include one or more components and/or sub-modules. As those skilled in the art will recognize, these components and sub-modules may be implemented by employing hardware (e.g., in the form of circuitry such as application specific integrated circuit or ASIC, field programmable gate array or FPGA, or other types of circuitry), software, a combination of both hardware and software, or a general purpose computing device 10 executing instructions included in a signal-bearing medium. In various embodiments, computing device 10 may include an events data acquisition module 102, an events pattern determination module 104, a hypothesis development module 106, an action execution module 108, a network interface 120 (e.g., network interface card or NIC), a user interface 122 (e.g., a display monitor, a touchscreen, a keypad or keyboard, a mouse, an audio system including a microphone and/or speakers, an image capturing system including digital and/or video camera, and/or other types of interface devices), one or more applications 126 (e.g., a web 2.0 application, a voice recognition application, and/or other applications that may be stored in a memory 140), and/or memory 140, which may include one or more existing hypothesis 80 and/or historical data 82.

The events data acquisition module 102 may be configured to, among other things, acquire events data 60* from one or more distinct sources. The events data 60* to be acquired by the events data acquisition module 102 may include at least data indicating incidence of a first one or more reported events 61* and data indicating incidence of a second one or more reported events 62*. At least one of the first one or more reported events 61* and the second one or more reported events 62* may be associated with a user 20*. The events data acquisition module 102 may also be designed to acquire data indicating incidence of a third one or more reported events 63* and other data indicating additional reported events from various sources.

Figure 2A:
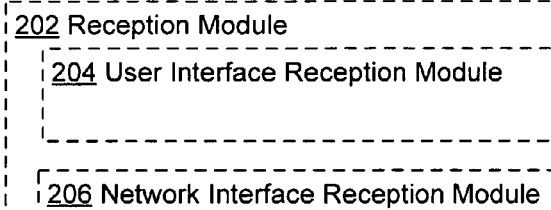
FIG. 2a shows another perspective of the events data acquisition module 102 of the computing device 10 of FIG. 1b.

Referring now to FIG. 2a illustrating particular implementations of the events data acquisition module 102 of the computing device 10 of FIG. 1b. The events data acquisition module 102 may include a reception module 202 for receiving at least one of the data indicating incidence of the first one or more reported events 61* and the data indicating incidence of the second one or more reported events 62*. The reception module 202 may further include a user interface reception module 204 and/or a network interface reception module 206. The user interface reception module 204 may be configured to receive, via a user interface 122, the events data 60* including at least one of the data indicating incidence of the first one or more reported events 61* and the data indicating incidence of the second one or more reported events 62*. In contrast, the network interface reception module 206 may be configured to receive (e.g., via network interface 120) from a wireless and/or wired network 40 the events data 60* including at least one of the data indicating incidence of the first one or more reported events 61* and the data indicating incidence of the second one or more reported events 62*.

The events pattern determination module 104 of the computing device 10 of FIG. 1b may be configured to, among other things, determine an events pattern based selectively on the incidences of the first one or more reported events and the second one or more reported events as indicted by the acquired events data 60*. In various implementations, the events pattern to be determined may at least indicate one or more spatial or sequential (e.g., time or temporal) relationships or links between the first one or more reported events and the second one or more reported events.

Figure 2B:
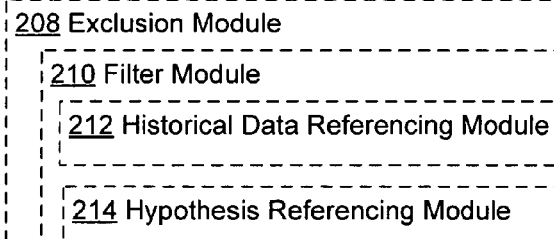
FIG. 2b shows another perspective of the events pattern determination module 104 of the computing device 10 of FIG. 1b.

FIG. 2b illustrates particular implementations of the events pattern determination module 104 of FIG. 1b. As illustrated, the events pattern determination module 104 may include an exclusion module 208 configured to exclude from the determination of the events pattern, noise data such as a third one or more reported events (e.g., data indicating incidence of a third one or more reported events 63*). In various implementations, the exclusion module 208 may further include a filter module 210 configured to filter the events data 60* to filter out noise data including the data indicating incidence of a third one or more reported events 63*. The filter module 210 may also include a historical data referencing module 212 and/or a hypothesis referencing module 214. The historical data referencing module 212 may be designed to reference historical data 82 to facilitate the filter module 210 in order to filter out noise data (e.g., data relating to reported events that are not relevant to the development of a hypothesis) from the events data 60*. In various implementations, the historical data 82 to be referenced may identify and link or associate at least two event types (e.g., a subjective user state and a subjective observation). In contrast, the hypothesis referencing module 214 may be designed to reference an existing hypothesis 80 to facilitate the filter module 210 to filter the events data 60*. In various implementations, the existing hypothesis 80 to be referenced may be specific to the user 20* or to a subgroup of the general population, the user 20* being part of the subgroup.

The hypothesis development module 106 of the computing device 10 of FIG. 1b may be configured to, among other things, develop a hypothesis associated with the user 20* based, at least in part, on the events pattern determined by the events pattern determination module 104. In various implementations, the development of the hypothesis may involve creating a new hypothesis or updating or refining an existing hypothesis 80. The hypothesis to be developed may indicate one or more relationships (e.g., spatial or sequential relationships) between a first one or more event types and a second one or more event types. In various implementations, the hypothesis to be developed may also indicate the strength or weakness of the hypothesis.

Figure 2C:
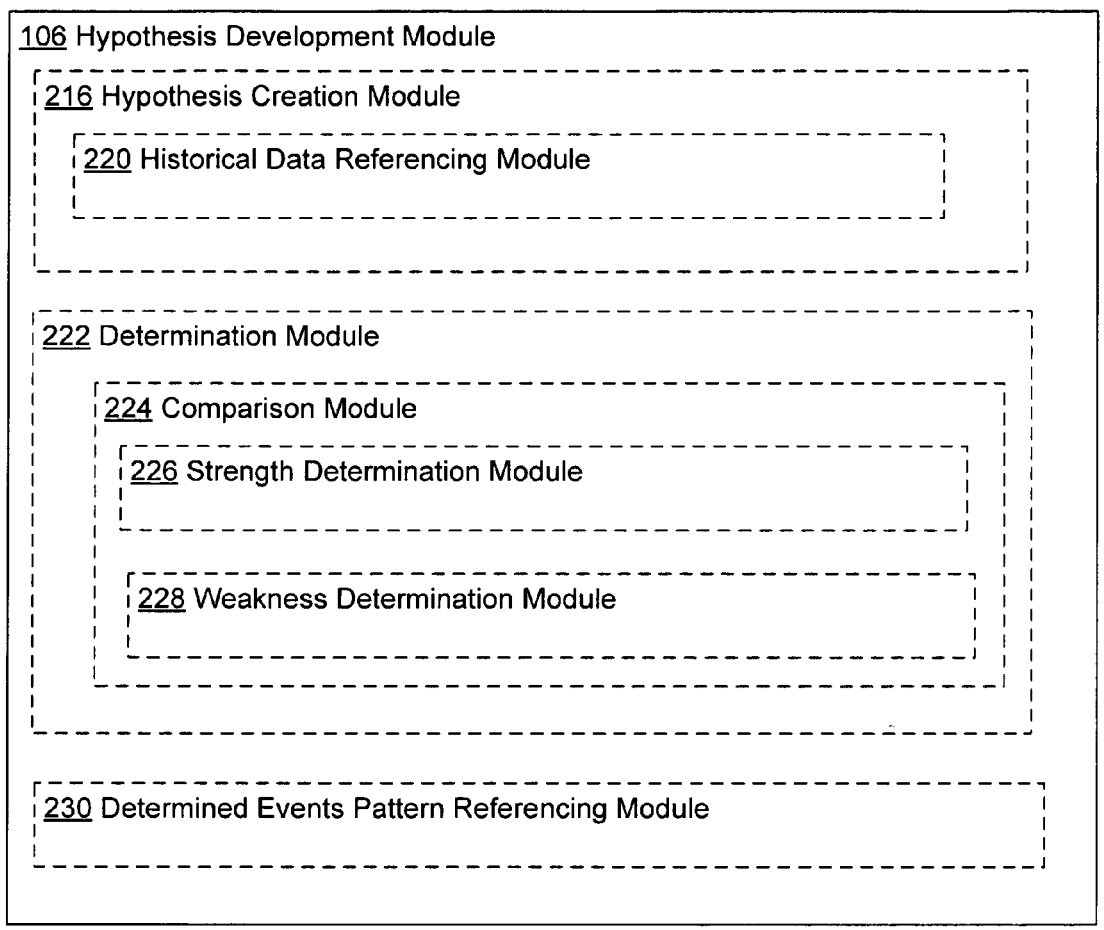
FIG. 2c shows another perspective of the hypothesis development module 106 of the computing device 10 of FIG. 1b.

FIG. 2c illustrates particular implementations of the hypothesis development module 106 of FIG. 1b. As illustrated, the hypothesis development module 106 may include a hypothesis creation module 216 configured to create a hypothesis based, at least in part, on the determined events pattern (e.g., the first one or more reported events and the second one or more reported events associated with the events pattern) and based on historical data 82 (e.g., historical data 82 that may be particular to the user 20*. The hypothesis creation module 216 may further include a historical data referencing module 220 configured to reference historical data 82 in order to facilitate in the creation of a hypothesis by the hypothesis creation module 216.

In various implementations, the hypothesis development module 106 may include a determination module 222 to facilitate in the further development of an existing hypothesis 80. In particular, the determination module 222 may be configured to determine whether the events pattern determined by, for example, the events pattern determination module 104 supports an existing hypothesis 82 associated with the user 20*. The determination module 222 may further include a comparison module 224 designed to compare the events pattern determined by, for example, the events pattern determination module 104 to an events pattern associated with the existing hypothesis 80 (e.g., an events pattern that links a first one or more event types with a second one or more event types) to determine whether the determined events pattern supports the existing hypothesis 80.

The comparison module 224 may also include a strength determination module 226 and/or a weakness determination module 228. In various implementations, the strength determination module 226 may be designed to determine the strength (e.g., soundness) of the existing hypothesis 80 associated with the user 20* based, at least in part on the comparison made by the comparison module 224. In particular, the strength determination module 226 may determine the strength of the relationship (or link) between a first one or more event types and a second one or more event types identified by the existing hypothesis 80 based on the comparison made by the comparison module 224. Note that if the determined events pattern exactly or substantially matches the events pattern associated with the existing hypothesis 80, then that may lead to the conclusion that the existing hypothesis 80 is relatively sound.

In contrast, the weakness determination module 228 may be designed to determine the weakness of the existing hypothesis 80 associated with the user 20* based, at least in part on the comparison made by the comparison module 224. In particular, the weakness determination module 228 may determine the weakness of the relationship (or link) between a first one or more event types and a second one or more event types identified by the existing hypothesis 82 based on the comparison made by the comparison module 224. Note that if the determined events pattern is completely or substantially dissimilar to the events pattern associated with the existing hypothesis 80, then that may lead to the conclusion that the existing hypothesis 80 is relatively weak. The strength or weakness relating the existing hypothesis 80, as determined by the strength determination module 226 or the weakness determination module 228, may be added to the existing hypothesis 80 to further develop or refine the existing hypothesis 80.

In various implementations, the hypothesis development module 106 may include a determined events pattern referencing module 230 configured to reference events pattern that have been determined by, for example, the events pattern determination module 104. Such referencing of the determined events pattern may facilitate the hypothesis development module 106 in developing a hypothesis associated with the user 20*.

Figure 2D:
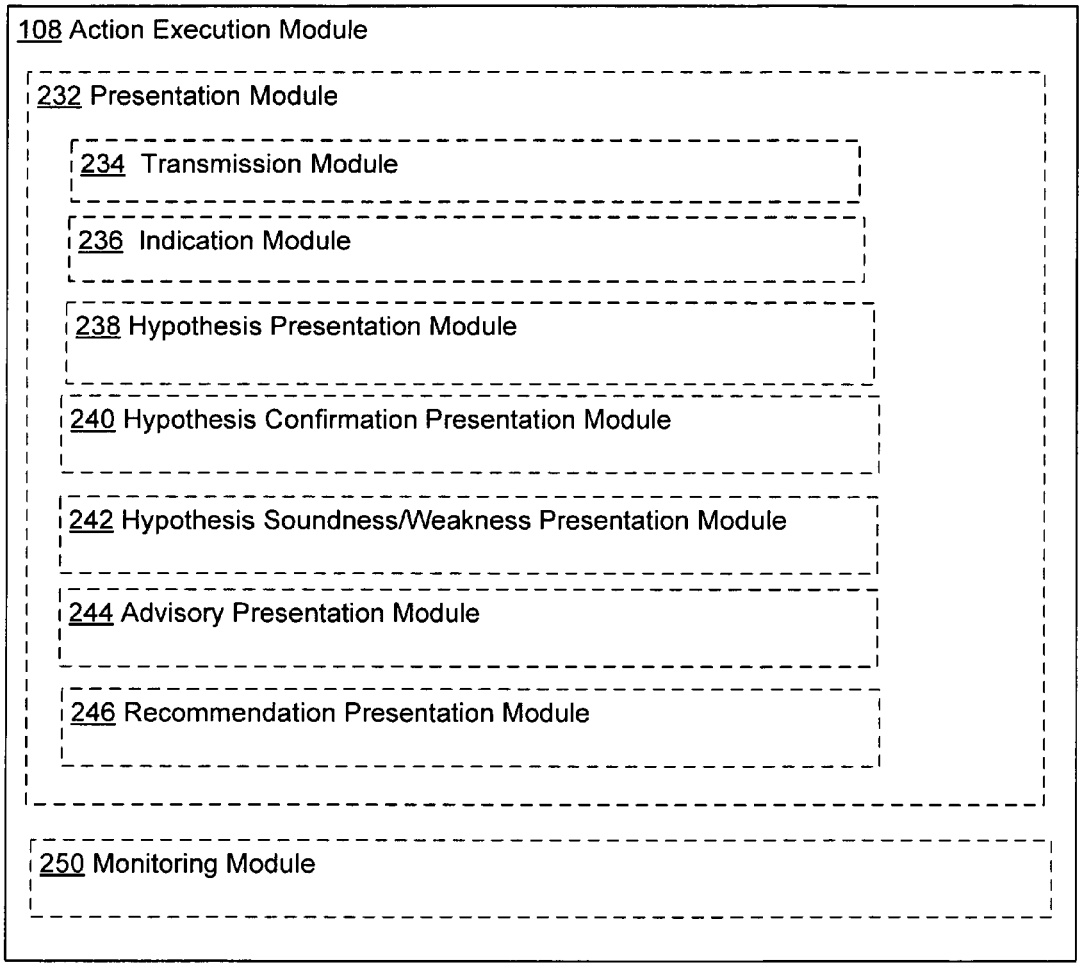
FIG. 2d shows another perspective of the action execution module 108 of the computing device 10 of FIG. 1b.

The action execution module 108 of the computing device 10 may be configured to execute one or more actions in response to, for example, the hypothesis development module 106 developing the hypothesis. Referring now to FIG. 2d illustrating particular implementations of the action execution module 108 of FIG. 1b. In various implementations, the action execution module 108 may include a presentation module 232 that may be configured to present (e.g., transmit via a network interface 120 or to indicate via a user interface 122) one or more results of the development of, for example, the hypothesis by the hypothesis development module 106. The presentation module 232 may further include one or more sub-modules including, for example, a transmission module 234, an indication module 236, a hypothesis presentation module 238, a hypothesis confirmation presentation module 240, a hypothesis soundness/weakness presentation module 242, an advisory presentation module 244, and/or a recommendation presentation module 246.

The transmission module 234 may be designed to, for example, transmit the one or more results of the developing of the hypothesis via a wireless and/or wired network 40. In various implementations, the one or more results 90 may be transmitted to the user 20*, one or more third parties (e.g., one or more third party sources 50), and/or to one or more remote network devices such as one or more network servers 36. In contrast, the indication module 236 may be designed to, for example, indicate the one or more results 90 via a user interface 122. The hypothesis presentation module 238 may be configured to present (e.g., transmit or indicate) the hypothesis developed by, for example, the hypothesis development module 106. In contrast, the hypothesis confirmation presentation module 240 may be configured to present (e.g., transmit or indicate) an indication of a confirmation of the hypothesis (e.g., existing hypothesis 80).

The hypothesis soundness/weakness presentation module 242 may be configured to present (e.g., transmit or indicate) an indication of the soundness or weakness of the hypothesis. Note that the words "soundness" and "strength" have been used interchangeably in reference to a hypothesis and therefore, are synonymous unless indicated otherwise. The advisory presentation module 244 may be configured to, among other things, presenting (e.g., transmit or indicate) an advisory of one or more past events. The recommendation presentation module 246 may be configured to present a recommendation for a future action based, for example, on the hypothesis.

In various implementations, the action execution module 108 may include a monitoring module 250 that may be configured to, among other things, monitor reported events. The monitoring of the reported events may involve determining whether the reported events include events that match or substantially match the types of events identified by the hypothesis. Upon detecting such events, additional actions may be taken such as soliciting for additional events data 60* in order to confirm, for example, the veracity of the hypothesis or generating an advisory to the user 20* or to one or more third party sources 50 regarding, for example, the possibility of the pattern of events identified by the hypothesis occurring.

Figure 2E:
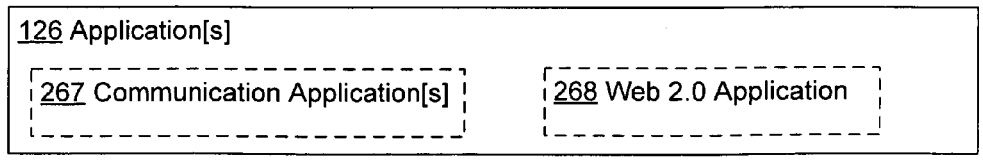
FIG. 2e shows another perspective of the one or more applications 126 of the computing device 10 of FIG. 1b.

FIG. 2e depicts particular implementations of the one or more applications 126 of the computing device 10 of FIG. 1b. The one or more applications 126 may include, for example, one or more communication applications 267 (e.g., text messaging application, instant messaging application, email application, voice recognition system, and so forth) and/or Web 2.0 application 268 to facilitate in communicating via, for example, the World Wide Web. In various implementations, the one or more applications 126 may be stored in the memory 140.

The network interface 120 of the computing device 10 may be a device designed to interface with a wireless and/or wired network 40. Examples of such devices include, for example, a network interface card (NIC) or other interface devices or systems for communicating through at least one of a wireless network or wired network 40. The user interface 122 of the computing device 10 may comprise any device that may interface with a user 20b. Examples of such devices include, for example, a keyboard, a display monitor, a touchscreen, a microphone, a speaker, an image capturing device such as a digital or video camera, a mouse, and so forth.

The memory 140 of the computing device 10 may include any type of volatile or non-volatile device used to store data. Examples of a memory 140 include, for example, a mass storage device, read only memory (ROM), programmable read only memory (PROM), erasable programmable read-only memory (EPROM), random access memory (RAM), flash memory, synchronous random access memory (SRAM), dynamic random access memory (DRAM), and so forth.

The various features and characteristics of the components, modules, and sub-modules of the computing device 10 presented thus far will be described in greater detail with respect to the processes and operations to be described herein.

Figure 3:
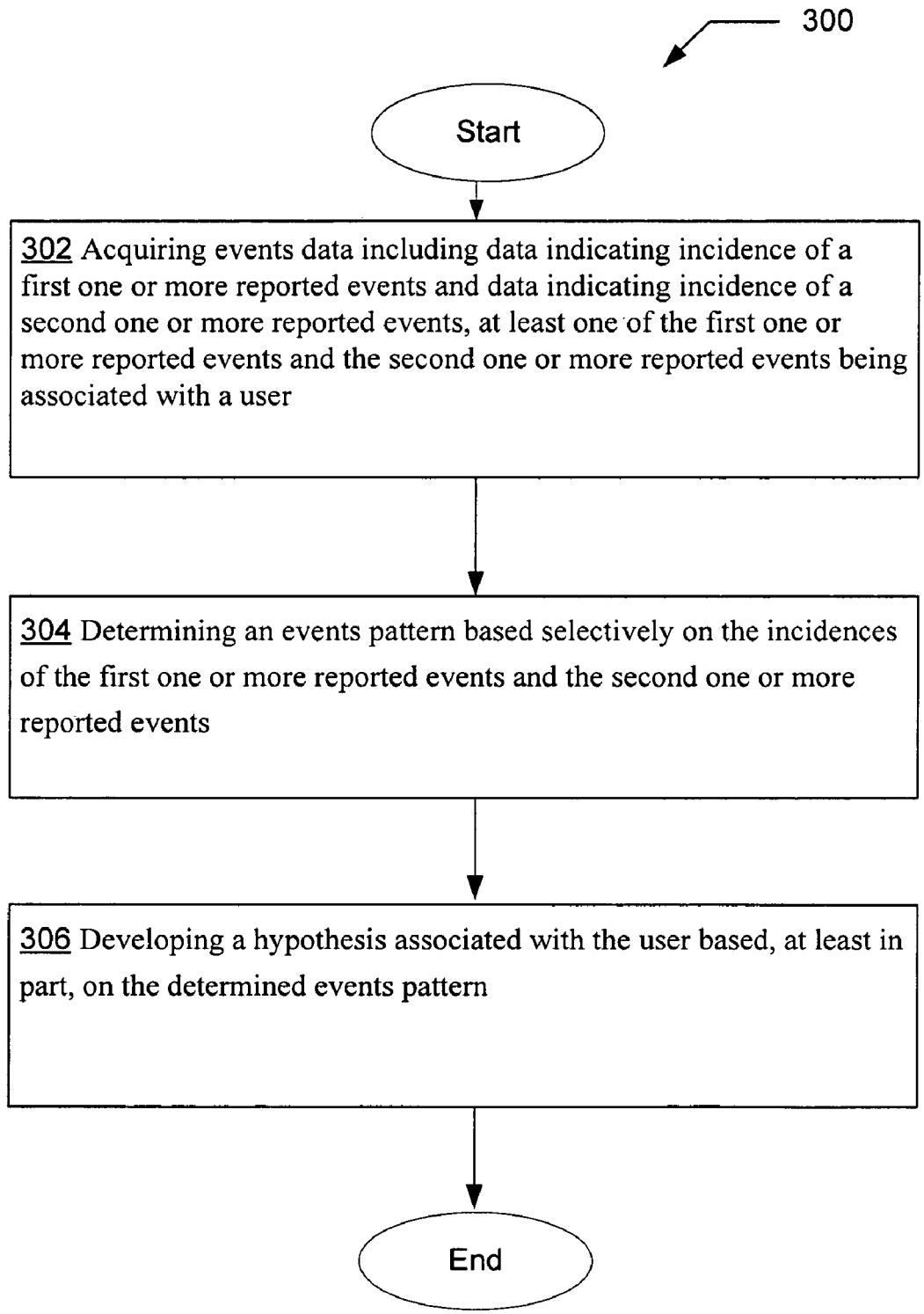
FIG. 3 is a high-level logic flowchart of a process.

FIG. 3 illustrates an operational flow 300 representing example operations related to, among other things, hypothesis development based, at least in part, on selective reported events. In some embodiments, the operational flow 300 may be executed by, for example, the computing device 10 of FIG. 1b, which may be a server or a standalone device.

In FIG. 3 and in the following figures that include various examples of operational flows, discussions and explanations may be provided with respect to the above-described exemplary environment of FIGS. 1a and 1b, and/or with respect to other examples (e.g., as provided in FIGS. 2a-2e) and contexts. However, it should be understood that the operational flows may be executed in a number of other environments and contexts, and/or in modified versions of FIGS. 1a, 1b, and 2a-2e. Also, although the various operational flows are presented in the sequence(s) illustrated, it should be understood that the various operations may be performed in different sequential orders other than those which are illustrated, or may be performed concurrently.

Further, in the following figures that depict various flow processes, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to an events data acquisition operation 302 for acquiring events data including data indicating incidence of a first one or more reported events and data indicating incidence of a second one or more reported events, at least one of the first one or more reported events and the second one or more reported events being associated with a user. For instance, the events data acquisition module 102 of the computing device 10 acquiring (e.g., acquiring from a user 20*, from one or more third party sources 50, from one or more sensors 35, and/or from memory 140) events data 60* including data indicating incidence of a first one or more reported events 61* and data indicating incidence of a second one or more reported events 62*, at least one of the first one or more reported events (e.g., subjective user states such as fatigue) and the second one or more reported events (e.g., objective occurrences such as going to sleep after midnight) being associated with a user 20*.

Next, operational flow 300 may include an events pattern determination operation 304 for determining an events pattern based selectively on the incidences of the first one or more reported events and the second one or more reported events. For instance, the events pattern determination module 104 of the computing device 10 determining an events pattern (e.g., a spatial events pattern or a time/temporal sequential events pattern) based selectively (e.g., by disregarding or filtering out non-relevant events data) on the incidences of the first one or more reported events (e.g., objective occurrences such as a user 20* meeting with the boss) and the second one or more reported events (e.g., subjective observations such as a third party observing that the user 20* appears to be angry).

Finally, operational flow 300 may include a hypothesis development operation 306 for developing a hypothesis associated with the user based, at least in part, on the determined events pattern. For instance, the hypothesis development module 106 of the computing device 10 developing a hypothesis (e.g., creating a new hypothesis or further developing an existing hypothesis 80) associated with the user 20* based, at least in part, on the events pattern determined, for example, by the events pattern determination module 104.

Figure 4A:
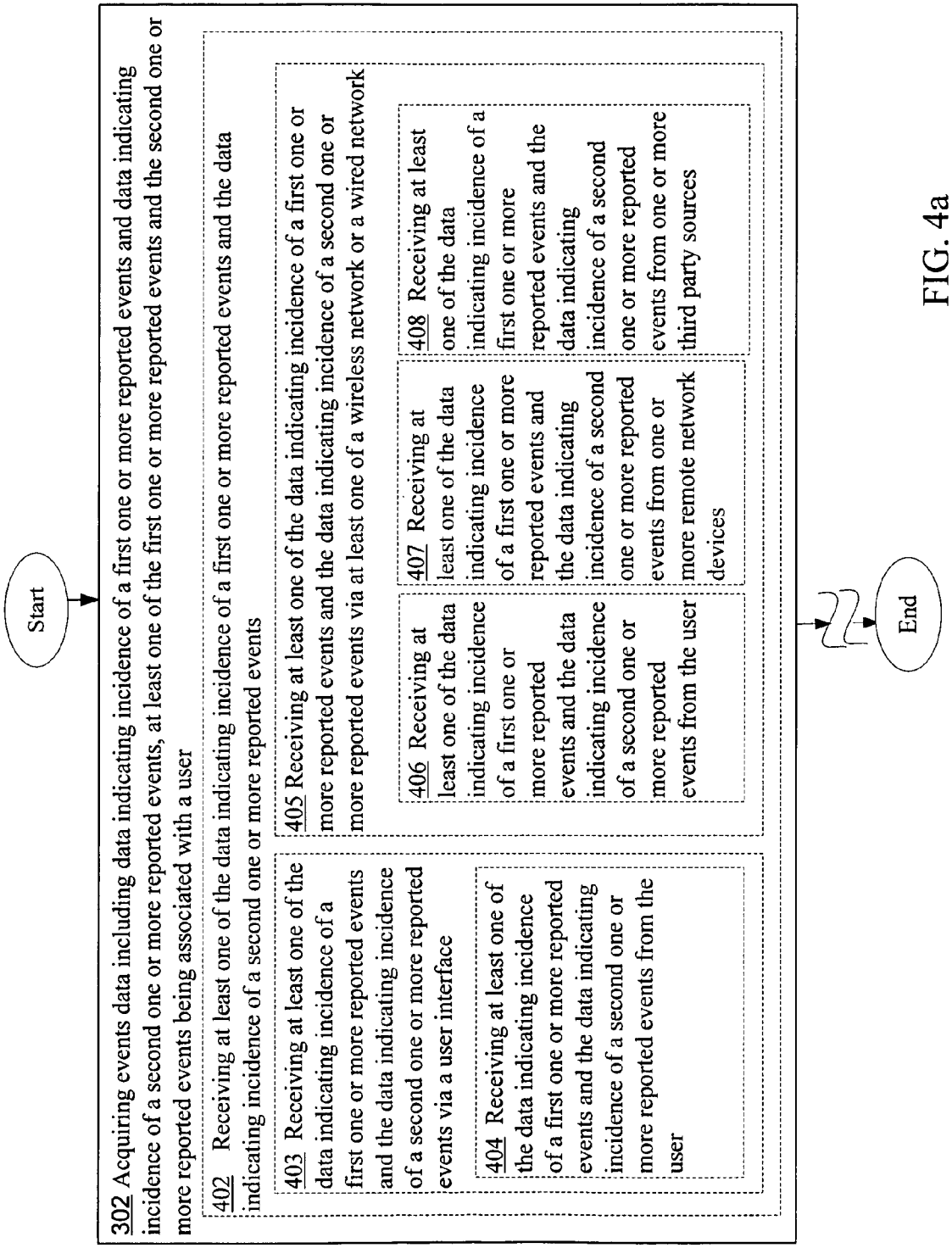
FIG. 4a is a high-level logic flowchart of a process depicting alternate implementations of the events data acquisition operation 302 of FIG. 3.

In various implementations, the events data acquisition operation 302 of FIG. 3 may be executed in a number of different ways as will be illustrated in FIGS. 4a, 4b, 4c, 4d, 4e, 4f, 4g, 4h, and 4i. For example, in some implementations, the events data acquisition operation 302 may include a reception operation 402 for receiving at least one of the data indicating incidence of a first one or more reported events and the data indicating incidence of a second one or more reported events as depicted in FIG. 4a. For instance, the reception module 202 of the computing device 10 receiving (e.g., via the network interface 120 or via the user interface 122) at least one of the data indicating incidence of a first one or more reported events 61* and the data indicating incidence of a second one or more reported events 62*.

In various implementations, the reception operation 402 may be performed in a number of different ways depending on the particular circumstances. For example, in some implementations, the reception operation 402 may include an operation 403 for receiving at least one of the data indicating incidence of a first one or more reported events and the data indicating incidence of a second one or more reported events via a user interface as depicted in FIG. 4a. For instance, the user interface reception module 204 (see FIG. 2a) of the computing device 10 receiving at least one of the data indicating incidence of a first one or more reported events 61a and the data indicating incidence of a second one or more reported events 62a via a user interface 122 (e.g., a touchscreen, a keypad, a mouse, a microphone, and so forth).

Operation 403, in turn, may further include an operation 404 for receiving at least one of the data indicating incidence of a first one or more reported events and the data indicating incidence of a second one or more reported events from the user as depicted in FIG. 4a. For instance, the user interface reception module 204 of the computing device 10 receiving at least one of the data indicating incidence of a first one or more reported events 61a and the data indicating incidence of a second one or more reported events 62a from the user 20b.

In the same or different implementations, the reception operation 402 may include an operation 405 for receiving at least one of the data indicating incidence of a first one or more reported events and the data indicating incidence of a second one or more reported events via at least one of a wireless network or a wired network as depicted in FIG. 4a. For instance, the network interface reception module 206 of the computing device 10 receiving (e.g., in the form of one or more microblog entries, one or more status reports, one or more electronic messages, and so forth) at least one of the data indicating incidence of a first one or more reported events 61* and the data indicating incidence of a second one or more reported events 62* via at least one of a wireless network or a wired network 40.

Depending upon circumstances, the data indicating incidence of a first one or more reported events 61* and/or the data indicating incidence of a second one or more reported events 62* received via the wireless and/or a wired network 40 may be provided by one or more different sources. For example, in some implementations, operation 405 may include an operation 406 for receiving at least one of the data indicating incidence of a first one or more reported events and the data indicating incidence of a second one or more reported events from the user as depicted in FIG. 4a. For instance, the network interface reception module 206 of the computing device 10 receiving (e.g., via a network interface 120 such as a network interface card or "NIC") at least one of the data indicating incidence of a first one or more reported events 61a and the data indicating incidence of a second one or more reported events 62a from the user 20a.

In the same or different implementations, operation 405 may include an operation 407 for receiving at least one of the data indicating incidence of a first one or more reported events and the data indicating incidence of a second one or more reported events from one or more remote network devices as depicted in FIG. 4a. For instance, the network interfaced reception module 206 of the computing device 10 receiving (e.g., via a network interface 120 such as a NIC) at least one of the data indicating incidence of a first one or more reported events 61b and the data indicating incidence of a second one or more reported events 62b from one or more remote network devices (e.g., one or more sensors 35 and/or one or more network servers 36).

In the same or different implementations, operation 405 may include an operation 408 for receiving at least one of the data indicating incidence of a first one or more reported events and the data indicating incidence of a second one or more reported events from one or more third party sources as depicted in FIG. 4a. For instance, the network interface reception module 206 of the computing device 10 receiving (e.g., via a network interface 120 such as a NIC) at least one of the data indicating incidence of a first one or more reported events 61c and the data indicating incidence of a second one or more reported events 62c from one or more third party sources 50.

Figure 4B:
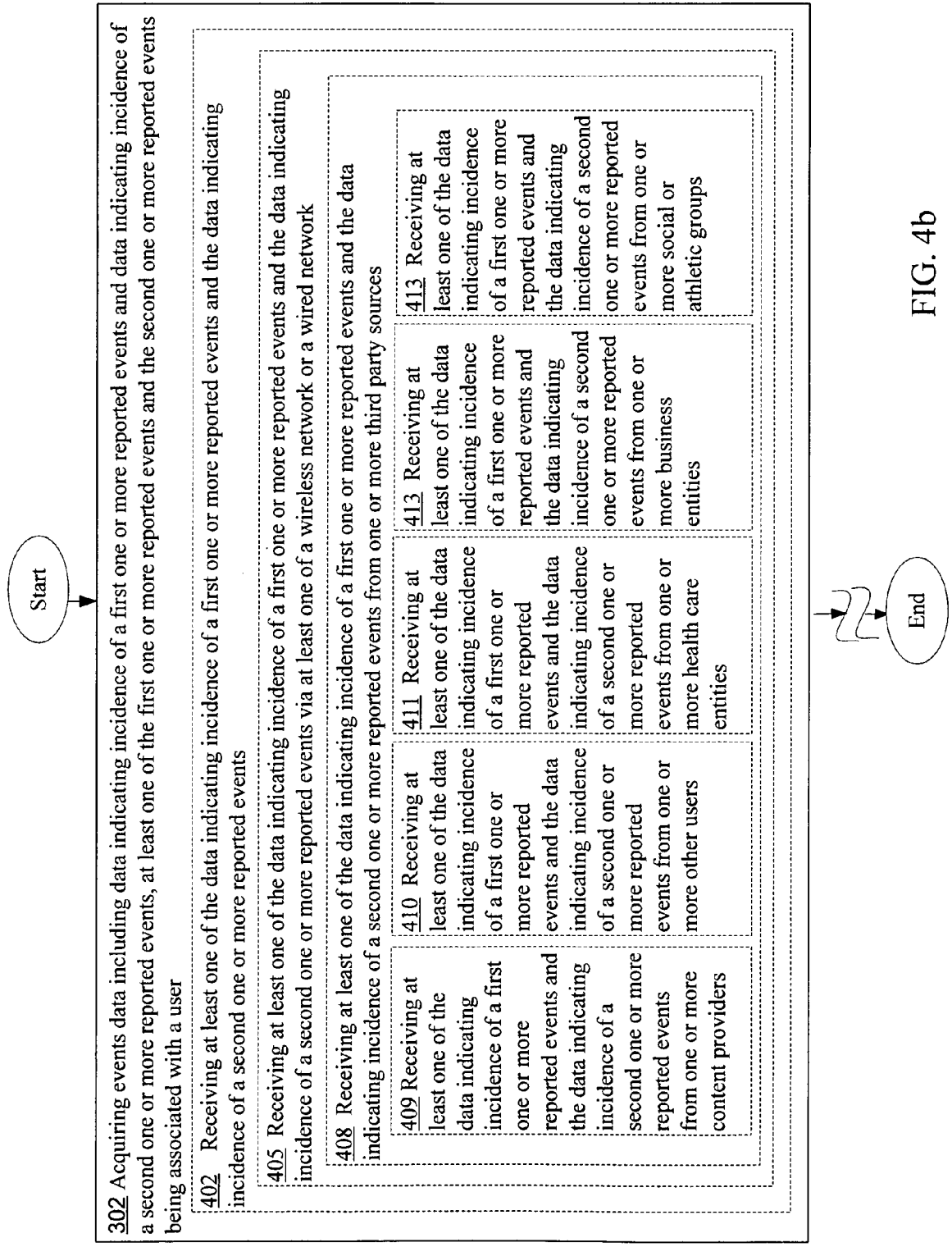
FIG. 4b is a high-level logic flowchart of a process depicting alternate implementations of the events data acquisition operation 302 of FIG. 3.

The one or more third party sources 50, as referred to above, may be in reference to various third parties (and/or the network devices that are associated with such parties). For example, in some implementations, operation 408 may include an operation 409 for receiving at least one of the data indicating incidence of a first one or more reported events and the data indicating incidence of a second one or more reported events from one or more content providers as depicted in FIG. 4b. For instance, the network interface reception module 206 of the computing device 10 receiving (e.g., via a network interface 120 such as a NIC) at least one of the data indicating incidence of a first one or more reported events 61c and the data indicating incidence of a second one or more reported events 62c from one or more content providers.

In some implementations, operation 408 may include an operation 410 for receiving at least one of the data indicating incidence of a first one or more reported events and the data indicating incidence of a second one or more reported events from one or more other users as depicted in FIG. 4b. For instance, the network interface reception module 206 of the computing device 10 receiving (e.g., via a network interface 120 such as a NIC) at least one of the data indicating incidence of a first one or more reported events 61c and the data indicating incidence of a second one or more reported events 62c from one or more other users (e.g., microbloggers).

In some implementations, operation 408 may include an operation 411 for receiving at least one of the data indicating incidence of a first one or more reported events and the data indicating incidence of a second one or more reported events from one or more health care entities as depicted in FIG. 4b. For instance, the network interface reception module 206 of the computing device 10 receiving (e.g., via a network interface 120 such as a NIC) at least one of the data indicating incidence of a first one or more reported events 61c and the data indicating incidence of a second one or more reported events 62c from one or more health care entities (e.g., hospital, medical or dental clinic, medical labs, and so forth).

In some implementations, operation 408 may include an operation 412 for receiving at least one of the data indicating incidence of a first one or more reported events and the data indicating incidence of a second one or more reported events from one or more business entities as depicted in FIG. 4b. For instance, the network interface reception module 206 of the computing device 10 receiving (e.g., via a network interface 120 such as a NIC) at least one of the data indicating incidence of a first one or more reported events 61c and the data indicating incidence of a second one or more reported events 62c from one or more business entities (e.g., merchants, internet websites, place of employment, and so forth).

In some implementations, operation 408 may include an operation 413 for receiving at least one of the data indicating incidence of a first one or more reported events and the data indicating incidence of a second one or more reported events from one or more social or athletic groups as depicted in FIG. 4b. For instance, the network interface reception module 206 of the computing device 10 receiving (e.g., via a network interface 120 such as a NIC) at least one of the data indicating incidence of a first one or more reported events 61c and the data indicating incidence of a second one or more reported events 62c from one or more social or athletic groups (e.g., sports clubs, PTA, and so forth).

Figure 4C:
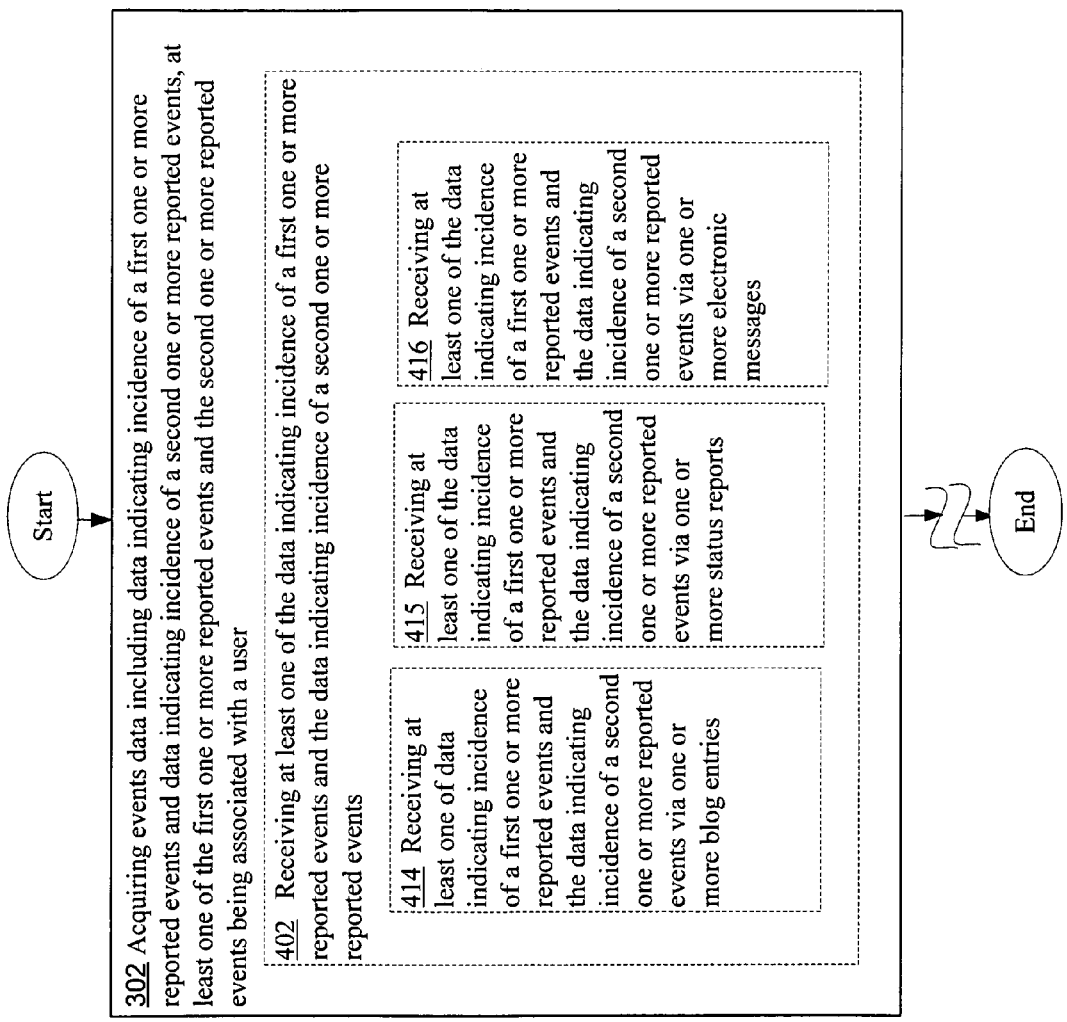
FIG. 4c is a high-level logic flowchart of a process depicting alternate implementations of the events data acquisition operation 302 of FIG. 3.

The data received during the reception operation 402 may be received in a variety of different forms. For example, in some implementations, the reception operation 402 may include an operation 414 for receiving at least one of the data indicating incidence of a first one or more reported events and the data indicating incidence of a second one or more reported events via one or more blog entries as depicted in FIG. 4c. For instance, the reception module 202 of the computing device 10 receiving at least one of the data indicating incidence of a first one or more reported events 61* and the data indicating incidence of a second one or more reported events 62* via one or more blog entries (e.g., microblog entries).

In the same or different implementations, the reception operation 402 may include an operation 415 for receiving at least one of the data indicating incidence of a first one or more reported events and the data indicating incidence of a second one or more reported events via one or more status reports as depicted in FIG. 4c. For instance, the reception module 202 of the computing device 10 receiving at least one of the data indicating incidence of a first one or more reported events 61* and the data indicating incidence of a second one or more reported events 62* via one or more status reports (e.g., social networking status reports).

In the same or different implementations, the reception operation 402 may include an operation 416 for receiving at least one of the data indicating incidence of a first one or more reported events and the data indicating incidence of a second one or more reported events via one or more electronic messages as depicted in FIG. 4c. For instance, the reception module 202 of the computing device receiving at least one of the data indicating incidence of a first one or more reported events 61* and the data indicating incidence of a second one or more reported events 62* via one or more electronic messages (e.g., text messages, email messages, instant messages, and so forth).

Figure 4D:
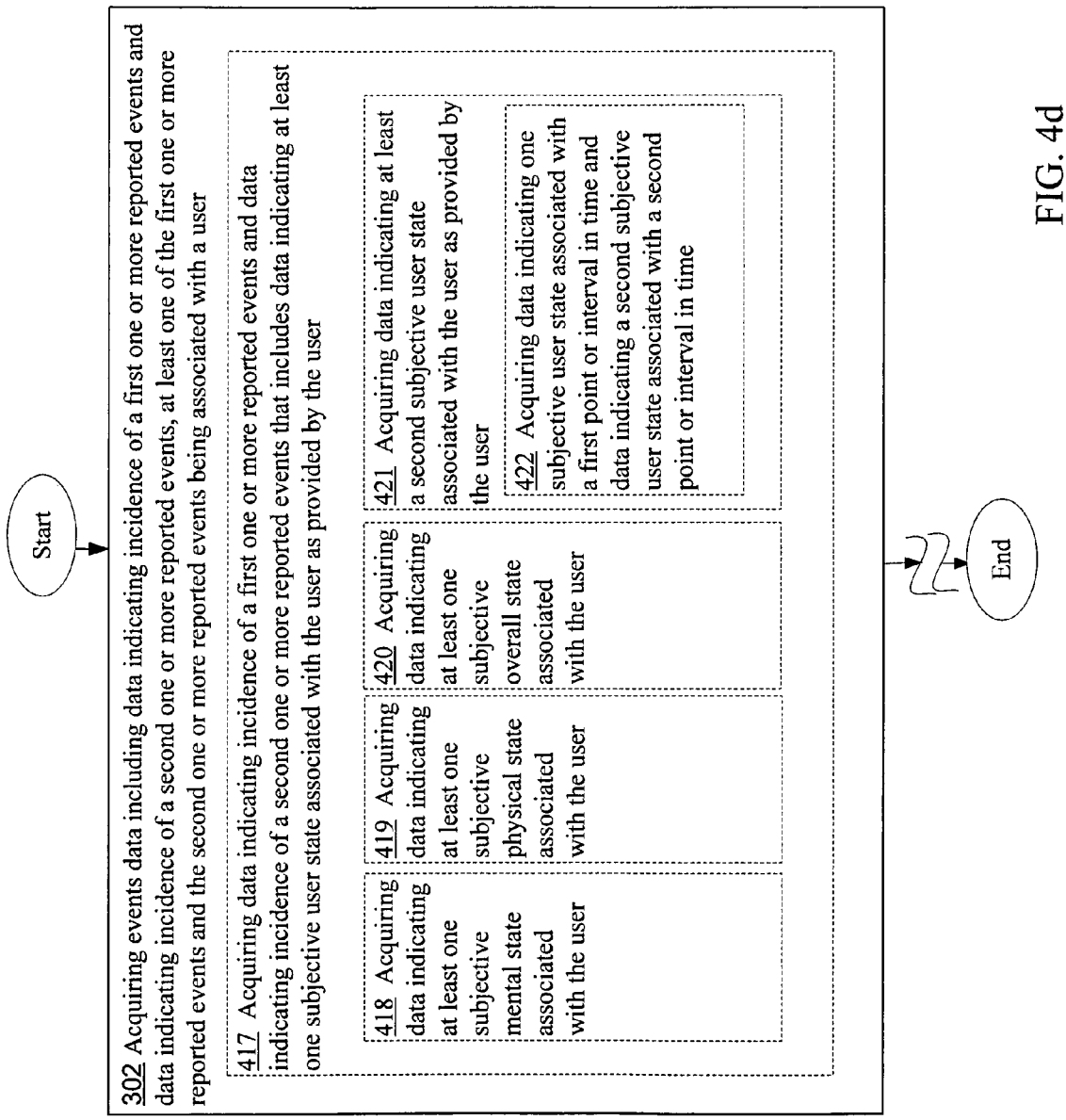
FIG. 4d is a high-level logic flowchart of a process depicting alternate implementations of the events data acquisition operation 302 of FIG. 3.

In various implementations, the data acquired through the events data acquisition operation 302 of FIG. 3 may include data that may indicate incidences of one or more subjective user states. For example, in some implementations, the events data acquisition operation 302 may include an operation 417 for acquiring data indicating incidence of a first one or more reported events and data indicating incidence of a second one or more reported events that includes data indicating at least one subjective user state associated with the user as provided by the user as depicted in FIG. 4d. For instance, the events data acquisition module 102 of the computing device 10 acquiring data indicating incidence of a first one or more reported events 61a and data indicating incidence of a second one or more reported events 62a that includes data indicating at least one subjective user state associated with the user 20* as provided by the user 20*(e.g., as provided by the user 20* via a user interface 122, via a wireless and/or wired network 40, via network servers 36, via memory 140, or through one or more third party sources 50).

One or more types of subjective user states may be indicated by the data acquired through operation 417. For example, in some implementations, operation 417 may include an operation 418 for acquiring data indicating at least one subjective mental state associated with the user as depicted in FIG. 4d. For instance, the events data acquisition module 102 of the computing device 10 acquiring data indicating at least one subjective mental state (e.g., anger, happiness, fatigued, alertness, jealousy, fear, nausea, and so forth) associated with the user 20*.

In the same or different implementations, operation 417 may include an operation 419 for acquiring data indicating at least one subjective physical state associated with the user as depicted in FIG. 4d. For instance, the events data acquisition module 102 of the computing device 10 acquiring data indicating at least one subjective physical state (e.g., sore ankle or upset stomach) associated with the user 20*.

In the same or different implementations, operation 417 may include an operation 420 for acquiring data indicating at least one subjective overall state associated with the user as depicted in FIG. 4d. For instance, the events data acquisition module 102 of the computing device 10 of acquiring data indicating at least one subjective overall state (e.g., "good," "bad," "well," and so forth) associated with the user 20*.

In some implementations, operation 417 may include an operation 421 for acquiring data indicating at least a second subjective user state associated with the user as provided by the user as depicted in FIG. 4d. For instance, the events data acquisition module 102 of the computing device 10 acquiring (e.g., by receiving from the user 20* or by retrieving from memory 140) data indicating at least a second subjective user state (e.g., a subjective mental state, a subjective physical state, or a subjective overall state) associated with the user 20* as provided by the user 20* (e.g., as provided by the user 20* via a user interface 122, via a wireless and/or wired network 40, via network servers 36, via memory 140, or through one or more third party sources 50).

In some implementations, operation 421 may further include an operation 422 for acquiring data indicating one subjective user state associated with a first point or interval in time and data indicating a second subjective user state associated with a second point or interval in time as depicted in FIG. 4d. For instance, the events data acquisition module 202 of the computing device 10 acquiring data indicating one subjective user state (e.g., elation) associated with a first point or interval in time and data indicating a second subjective user state (e.g., depression) associated with a second point or interval in time.

Figure 4E:
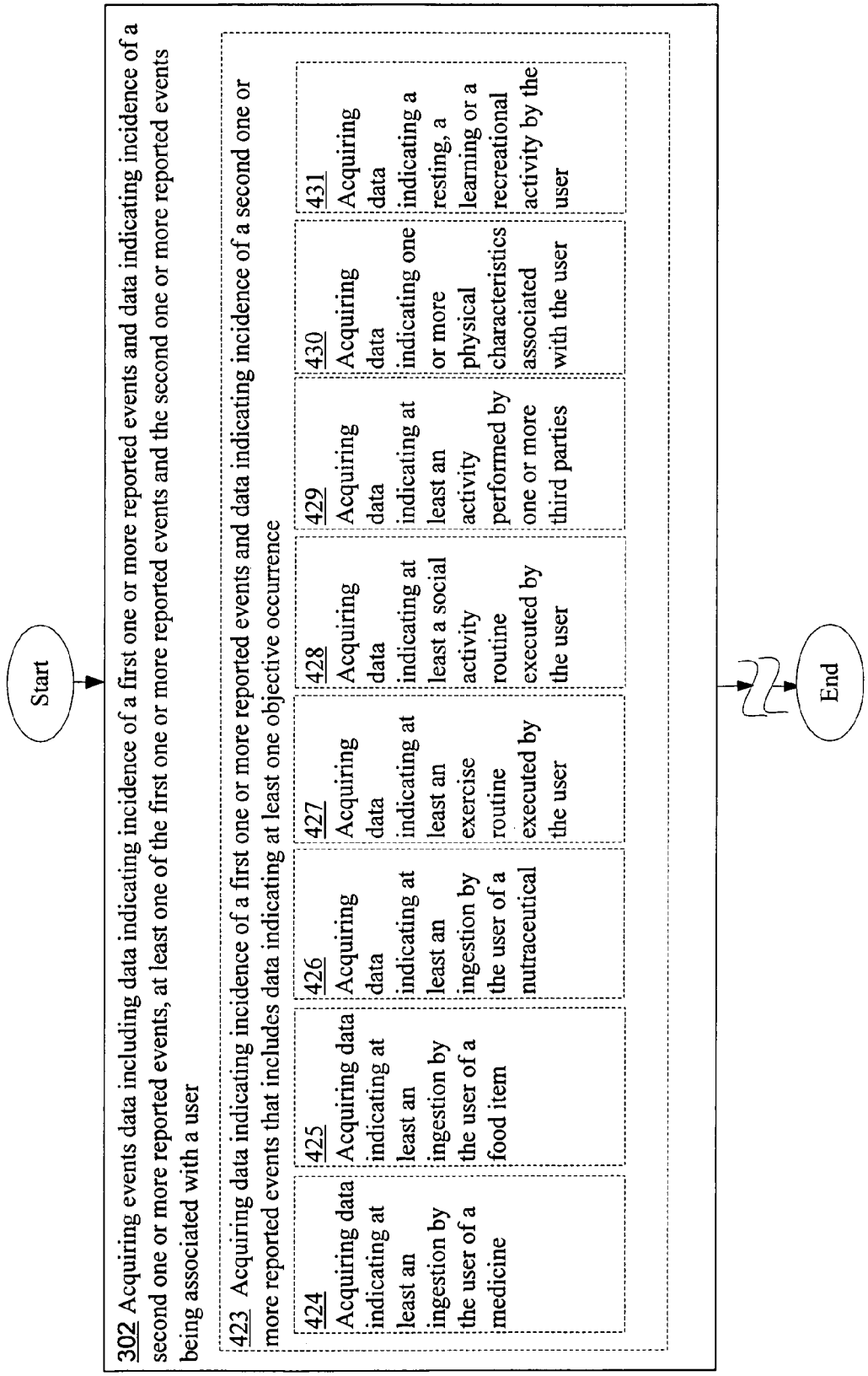
FIG. 4e is a high-level logic flowchart of a process depicting alternate implementations of the events data acquisition operation 302 of FIG. 3.

In various implementations, the data acquired through the events data acquisition operation 302 of FIG. 3 may include data that may indicate one or more objective occurrences. For example, in some implementations, the events data acquisition operation 302 may include an operation 423 for acquiring data indicating incidence of a first one or more reported events and data indicating incidence of a second one or more reported events that includes data indicating at least one objective occurrence as depicted in FIG. 4e. For instance, the events data acquisition module 102 of the computing device 10 acquiring data indicating incidence of a first one or more reported events 61* and data indicating incidence of a second one or more reported events 62* that includes data indicating at least one objective occurrence (e.g., an objectively observable activity performed by the user 20* or an objectively observable external event).

One or more types of objective occurrences may be indicated by the data acquired through operation 423. For example, in some implementations, operation 423 may include an operation 424 for acquiring data indicating at least an ingestion by the user of a medicine as depicted in FIG. 4e. For instance, the events data acquisition module 102 of the computing device 10 acquiring data indicating at least an ingestion by the user 20* of a medicine (e.g., a dose of aspirin).

In some implementations, operation 423 may include an operation 425 for acquiring data indicating at least an ingestion by the user of a food item as depicted in FIG. 4e. For instance, the events data acquisition module 102 of the computing device 10 acquiring data indicating at least an ingestion by the user 20* of a food item (e.g., 24 ounces of Filipino beer).

In some implementations, operation 423 may include an operation 426 for acquiring data indicating at least an ingestion by the user of a nutraceutical as depicted in FIG. 4e. For instance, the events data acquisition module 102 of the computing device 10 acquiring data indicating at least an ingestion by the user 20* of a nutraceutical (e.g., four ounces of red grapes).

Other types of activities executed by the user 20* or by one or more third parties (e.g., third party sources 50) may be indicated by data acquired during operation 423. For example, in some implementations, operation 423 may include an operation 427 for acquiring data indicating at least an exercise routine executed by the user as depicted in FIG. 4e. For instance, the events data acquisition module 102 of the computing device 10 acquiring data indicating at least an exercise routine executed by the user 20* (e.g., walking for 45 minutes). Note that the events data acquisition module 102 may be configured to acquire data indicating objectively observable activities of the user 20* or one or more third parties in various alternative implementations. In the same or different implementations, the events data acquisition module 102 may be configured to acquire data indicating objectively observable external events as will be illustrated in the following.

In some implementations, operation 423 may include an operation 428 for acquiring data indicating at least a social activity routine executed by the user as depicted in FIG. 4e. For instance, the events data acquisition module 102 of the computing device 10 acquiring data indicating at least a social activity routine executed by the user 20* (e.g., dinner with girlfriend).

In some implementations, operation 423 may include an operation 429 for acquiring data indicating at least an activity performed by one or more third parties as depicted in FIG. 4e. For instance, the events data acquisition module 102 of the computing device 10 acquiring data indicating at least an activity performed by one or more third parties (e.g., spouse leaving for a business trip).

In some implementations, operation 423 may include an operation 430 for acquiring data indicating one or more physical characteristics associated with the user as depicted in FIG. 4e. For instance, the events data acquisition module 102 of the computing device 10 acquiring data indicating one or more physical characteristics associated with the user 20* (e.g., blood pressure).

In some implementations, operation 423 may include an operation 431 for acquiring data indicating a resting, a learning, or a recreational activity by the user as depicted in FIG. 4e. For instance, the events data acquisition module 102 of the computing device 10 acquiring data indicating a resting (e.g., napping), a learning (e.g., attending a class or reading a book), or a recreational activity (e.g., golfing) by the user 20*.

Figure 4F:
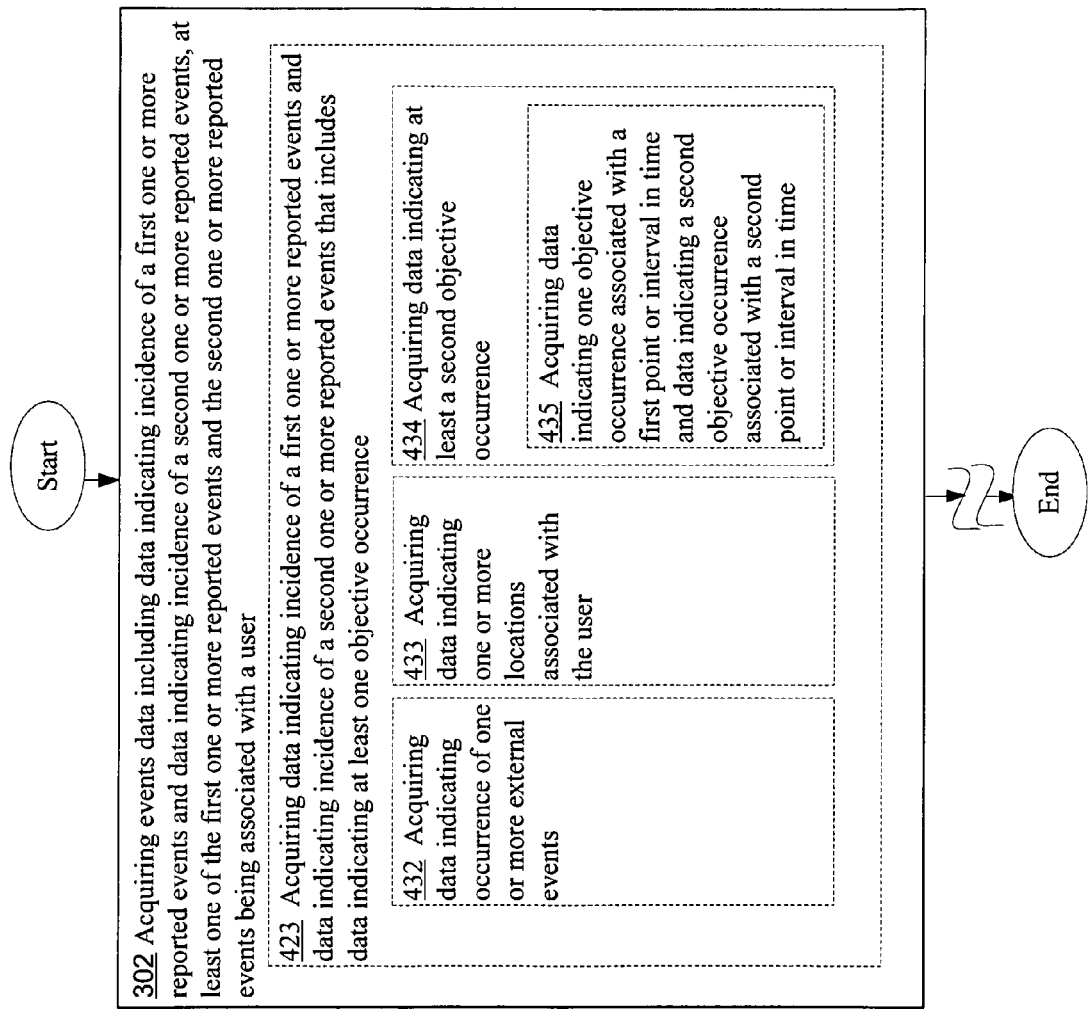
FIG. 4f is a high-level logic flowchart of a process depicting alternate implementations of the events data acquisition operation 302 of FIG. 3.

In some implementations, operation 423 may include an operation 432 for acquiring data indicating occurrence of one or more external events as depicted in FIG. 4f. For instance, the events data acquisition module 102 of the computing device 10 acquiring data indicating occurrence of one or more external events (e.g., weather or performance of favorite baseball team).

In some implementations, operation 423 may include an operation 433 for acquiring data indicating one or more locations associated with the user as depicted in FIG. 4f. For instance, the events data acquisition module 102 of the computing device 10 acquiring data indicating one or more locations associated with the user 20* (e.g., place of employment).

In some implementations, operation 423 may include an operation 434 for acquiring data indicating at least a second objective occurrence as depicted in FIG. 4f. For instance, the events data acquisition module 102 of the computing device 10 acquiring data indicating at least a second objective occurrence.

In various implementations, operation 434 may comprise of an operation 435 for acquiring data indicating one objective occurrence associated with a first point or interval in time and data indicating a second objective occurrence associated with a second point or interval in time as depicted in FIG. 4f. For instance, the events data acquisition module 102 of the computing device 10 acquiring data indicating one objective occurrence (e.g., eating ice cream) associated with a first point or interval in time and data indicating a second objective occurrence (e.g., high blood sugar level) associated with a second point or interval in time.

Figure 4G:
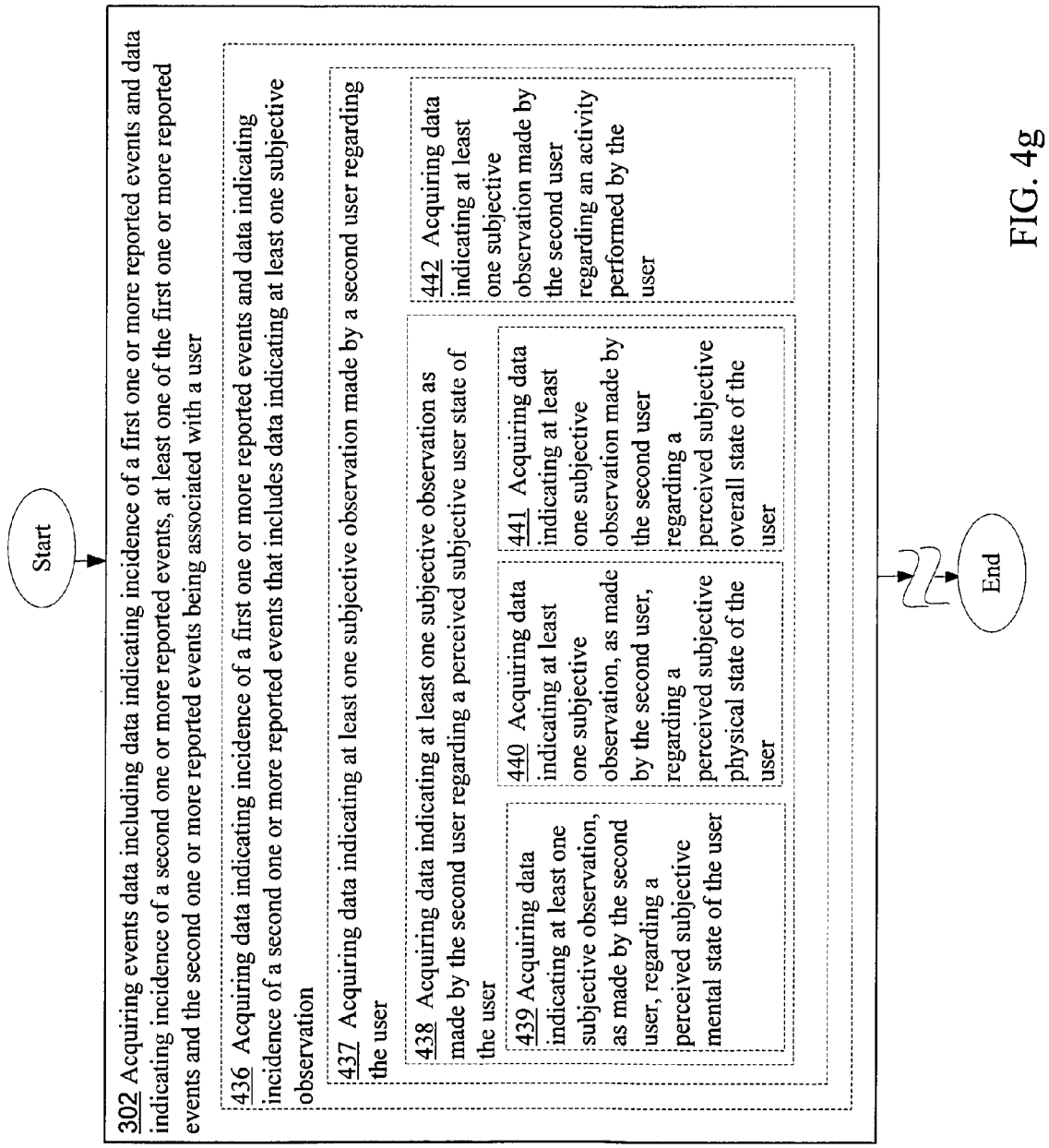
FIG. 4g is a high-level logic flowchart of a process depicting alternate implementations of the events data acquisition operation 302 of FIG. 3.

The data acquired in the events data acquisition operation 302 of FIG. 3 in various implementations may include data that indicates one or more subjective observations. For example, in some implementations, the events data acquisition operation 302 may include an operation 436 for acquiring data indicating incidence of a first one or more reported events and data indicating incidence of a second one or more reported events that includes data indicating at least one subjective observation as depicted in FIG. 4g. For instance, the events data acquisition module 102 of the computing device 10 acquiring data indicating incidence of a first one or more reported events 61* and data indicating incidence of a second one or more reported events 62* that includes data indicating at least one subjective observation (e.g., an observation made by a person regarding the perceived subjective user state of another person).

Note that although a subjective observation may be made by a particular person such as user 20*, the data that indicates the subjective observation may be provided by the user 20*, by one or more third party sources 50 (e.g., other users), by one or more remote network devices such as network servers 36, or by any other entities that may have access to such data. In other words, the user 20* who may have made the actual subjective observation may provide indication of his/her observation to other parties/entities that may ultimately disseminate such information.

In various implementations, operation 436 may include one or more additional operations. For example, in some implementations, operation 436 may include an operation 437 for acquiring data indicating at least one subjective observation made by a second user regarding the user as depicted in FIG. 4g. For instance, the events data acquisition module 102 of the computing device 10 acquiring data indicating at least one subjective observation (e.g., perceived unhappiness) made by a second user (e.g., third party source 50) regarding the user 20*.

Operation 437, in turn, may further include one or more additional operations. For example, in some implementations, operation 437 may include an operation 438 for acquiring data indicating at least one subjective observation, as made by the second user, regarding a perceived subjective user state of the user as depicted in FIG. 4g. For instance, the events data acquisition module 102 of the computing device 10 acquiring data indicating at least one subjective observation, as made by the second user (e.g., third party source 50), regarding a perceived subjective user state (e.g., happy) of the user 20*.

In various implementations, operation 438 may further comprise one or more operations. For example, in some implementations, operation 438 may include an operation 439 for acquiring data indicating at least one subjective observation, as made by the second user, regarding a perceived subjective mental state of the user as depicted in FIG. 4g. For instance, the events data acquisition module 102 of the computing device 10 acquiring data indicating at least one subjective observation, as made by the second user, regarding a perceived subjective mental state (e.g., anger) of the user 20*.

In some implementations, operation 438 may include an operation 440 for acquiring data indicating at least one subjective observation, as made by the second user, regarding a perceived subjective physical state of the user as depicted in FIG. 4g. For instance, the events data acquisition module 102 of the computing device 10 acquiring data indicating at least one subjective observation, as made by the second user, regarding a perceived subjective physical state (e.g., sore ankle) of the user 20*.

In some implementations, operation 438 may include an operation 441 for acquiring data indicating at least one subjective observation made by the second user regarding a perceived subjective overall state of the user as depicted in FIG. 4g. For instance, the events data acquisition module 102 of the computing device 10 acquiring data indicating at least one subjective observation, as made by the second user, regarding a perceived subjective overall state (e.g., "bad") of the user 20*.

In various implementations, operation 437 may include an operation 442 for acquiring data indicating at least one subjective observation made by the second user regarding an activity performed by the user as depicted in FIG. 4g. For instance, the events data acquisition module 102 of the computing device 10 acquiring data indicating at least one subjective observation made by the second user regarding an activity (e.g., ate too much for dinner) performed by the user 20*.

Figure 4H:
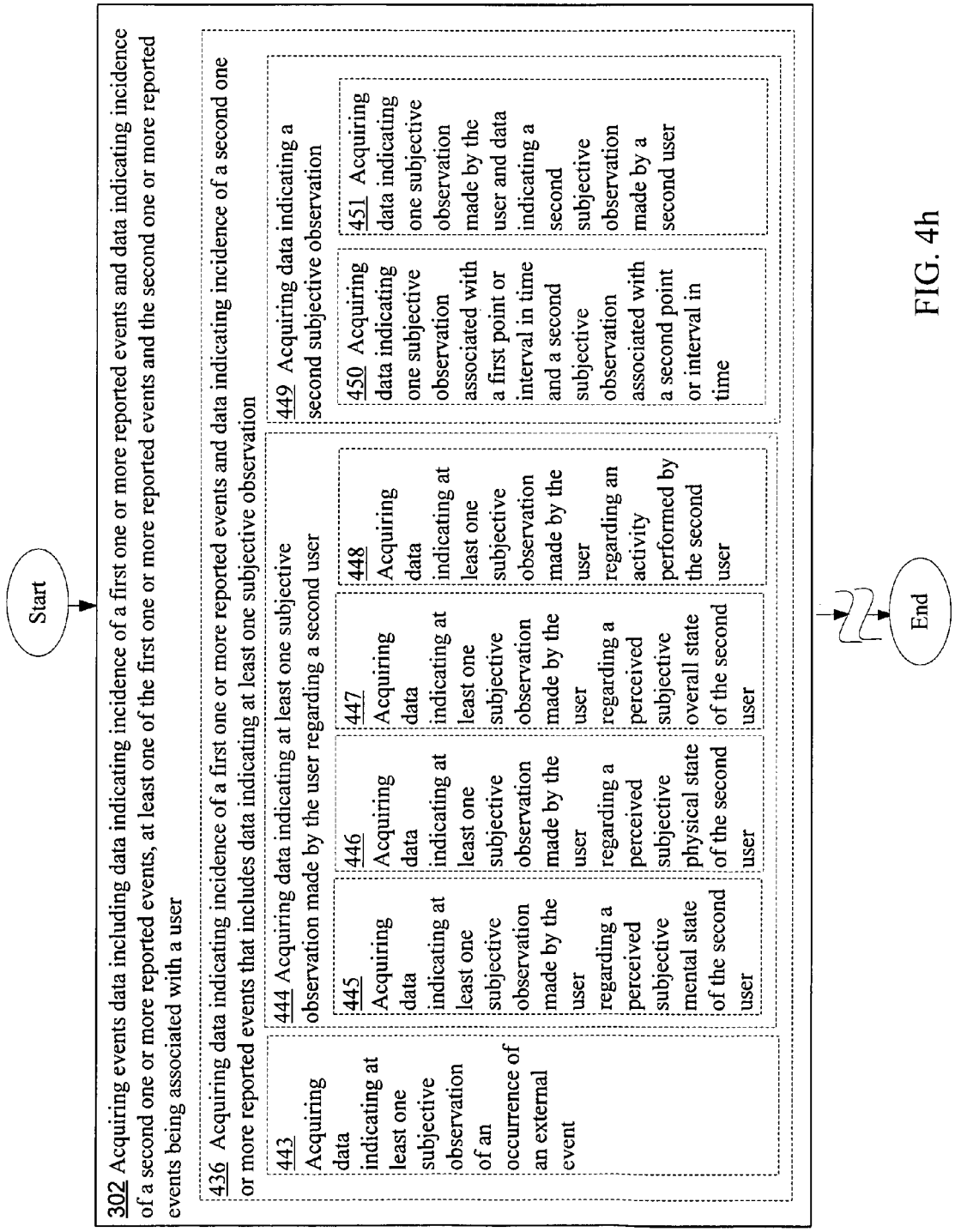
FIG. 4h is a high-level logic flowchart of a process depicting alternate implementations of the events data acquisition operation 302 of FIG. 3.

In various implementations, operation 436 may include an operation 443 for acquiring data indicating at least one subjective observation of an occurrence of an external event as depicted in FIG. 4h. For instance, the events data acquisition module 102 of the computing device 10 acquiring data indicating at least one subjective observation (e.g., as made by the user 20* or by a third party) regarding an occurrence of an external event (e.g., "good weather").

In some implementations, operation 436 may include an operation 444 for acquiring data indicating at least one subjective observation made by the user regarding a second user as depicted in FIG. 4h. For instance, the events data acquisition module 102 of the computing device 10 acquiring data indicating at least one subjective observation made by the user 20* regarding a second user (e.g., a third party source 50 such as another user). Various types of subjective observations regarding a second user may be indicated by the data acquired through operation 444.

For example, in some implementations, operation 444 may include an operation 445 for acquiring data indicating at least one subjective observation made by the user regarding a perceived subjective mental state of the second user as depicted in FIG. 4h. For instance, the events data acquisition module 102 of the computing device 10 acquiring data indicating at least one subjective observation made by the user 20* regarding a perceived subjective mental state of the second user (e.g., "he appears to be confused").

In the same or different implementations, operation 444 may include an operation 446 for acquiring data indicating at least one subjective observation made by the user regarding a perceived subjective physical state of the second user as depicted in FIG. 4h. For instance, the events data acquisition module 102 of the computing device 10 acquiring data indicating at least one subjective observation made by the user 20* regarding a perceived subjective physical state of the second user (e.g., "he appears to have a cramp").

In the same or different implementations, operation 444 may include an operation 447 for acquiring data indicating at least one subjective observation made by the user regarding a perceived subjective overall state of the second user as depicted in FIG. 4h. For instance, the events data acquisition module 102 of the computing device 10 acquiring data indicating at least one subjective observation made by the user 20* regarding a perceived subjective overall state of the second user (e.g., "he seems to be OK").

In the same or different implementations, operation 444 may include an operation 448 for acquiring data indicating at least one subjective observation made by the user regarding an activity performed by the second user as depicted in FIG. 4h. For instance, the events data acquisition module 102 of the computing device 10 acquiring data indicating at least one subjective observation made by the user 20* regarding an activity performed by the second user (e.g., "she exercised vigorously this morning"). Note that such an activity could be related to the behavior, facial expression, or any other physical activities of the second user.

In various implementations, operation 436 may include an operation 449 for acquiring data indicating a second subjective observation as depicted in FIG. 4h. For instance, the events data acquisition module 102 of the computing device 10 acquiring data indicating a second subjective observation (e.g., as made by the user 20* or by a third party source 50 such as another user).

In some implementations, operation 449 may include an operation 450 for acquiring data indicating one subjective observation associated with a first point or interval in time and a second subjective observation associated with a second point or interval in time as depicted in FIG. 4h. For instance, the events data acquisition module 102 of the computing device 10 acquiring data indicating one subjective observation (e.g., he exercised vigorously this morning) associated with a first point or interval in time and a second subjective observation (e.g., he looks very alert today) associated with a second point or interval in time.

In some implementations, operation 449 may include an operation 451 for acquiring data indicating one subjective observation made by the user and data indicating a second subjective observation made by a second user as depicted in FIG. 4h. For instance, the events data acquisition module 102 of the computing device 10 acquiring data indicating one subjective observation (e.g., "the weather is nice today") made by the user 20* and data indicating a second subjective observation (e.g., "the user appears to be happy today") made by a second user (e.g., a third party source 50).

Figure 4I:
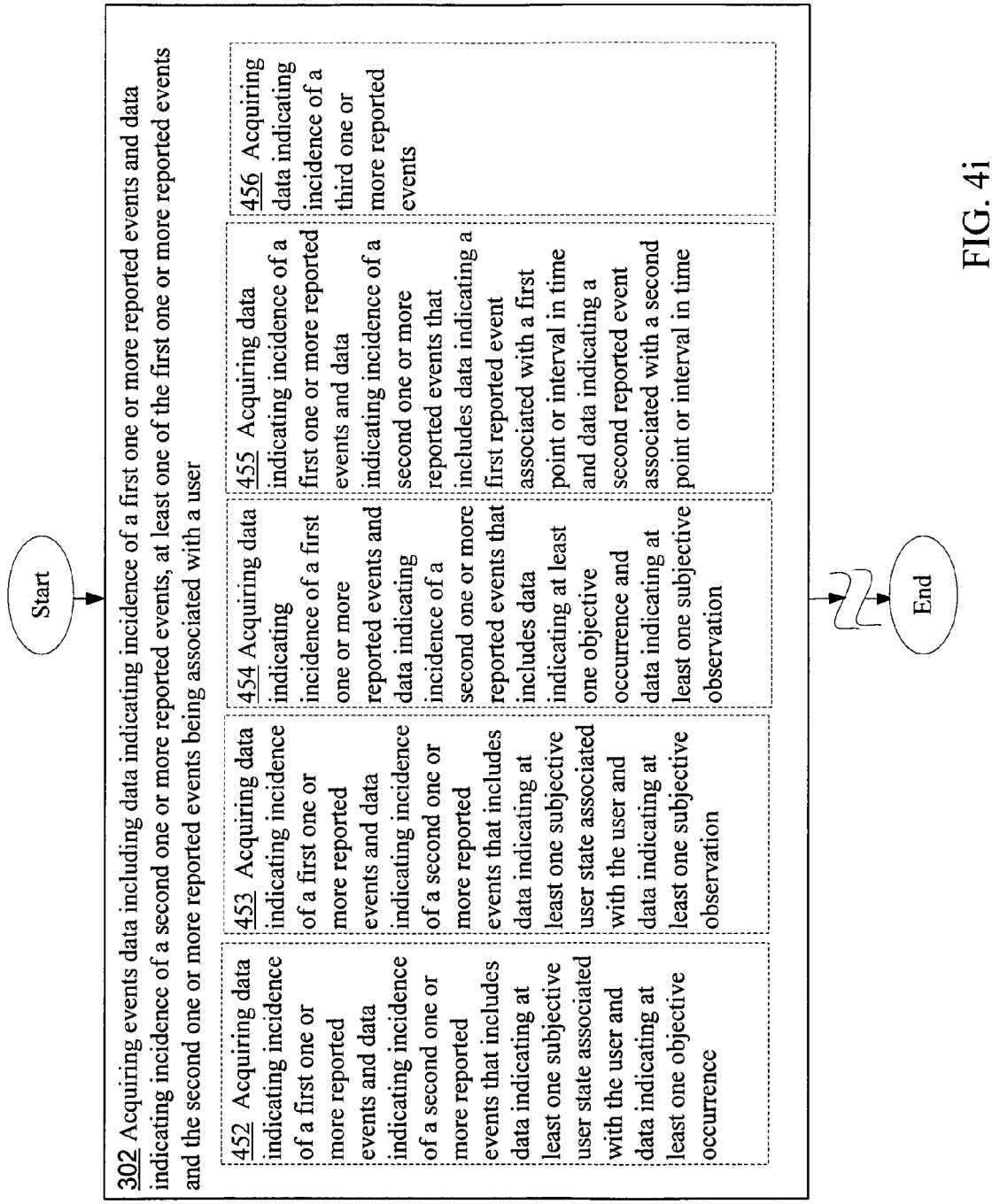
FIG. 4i is a high-level logic flowchart of a process depicting alternate implementations of the events data acquisition operation 302 of FIG. 3.

Referring back to the events data acquisition operation 302 of FIG. 3, in some implementations, the events data acquisition operation 302 may include an operation 452 for acquiring data indicating incidence of a first one or more reported events and data indicating incidence of a second one or more reported events that includes data indicating at least one subjective user state associated with the user and data indicating at least one objective occurrence as depicted in FIG. 4i. For instance, the events data acquisition module 102 of the computing device 10 acquiring data indicating incidence of a first one or more reported events 61* and data indicating incidence of a second one or more reported events 62* that includes data indicating at least one subjective user state (e.g., tension) associated with the user 20* and data indicating at least one objective occurrence (e.g., high blood pressure).

In some implementations, the events data acquisition operation 302 may include an operation 453 for acquiring data indicating incidence of a first one or more reported events and data indicating incidence of a second one or more reported events that includes data indicating at least one subjective user state associated with the user and data indicating at least one subjective observation as depicted in FIG. 4i. For instance, the events data acquisition module 102 of the computing device 10 acquiring data indicating incidence of a first one or more reported events 61* and data indicating incidence of a second one or more reported events 62* that includes data indicating at least one subjective user state (e.g., anxiety) associated with the user 20* and data indicating at least one subjective observation (e.g., "boss appears angry").

In some implementations, the events data acquisition operation 302 may include an operation 454 for acquiring data indicating incidence of a first one or more reported events and data indicating incidence of a second one or more reported events that includes data indicating at least one objective occurrence and data indicating at least one subjective observation as depicted in FIG. 4i. For instance, the events data acquisition module 102 of the computing device 10 acquiring data indicating incidence of a first one or more reported events 61* and data indicating incidence of a second one or more reported events 62* that includes data indicating at least one objective occurrence (e.g., high blood pressure) and data indicating at least one subjective observation (e.g., "the stock market performed poorly today").

In some implementations, the events data acquisition operation 302 may include an operation 455 for acquiring data indicating incidence of a first one or more reported events and data indicating incidence of a second one or more reported events that includes data indicating a first reported event associated with a first point or interval in time and data indicating a second reported event associated with a second point or interval in time as depicted in FIG. 4i. For instance, the events data acquisition module 102 of the computing device 10 acquiring data indicating incidence of a first one or more reported events 61* and data indicating incidence of a second one or more reported events 62* that includes data indicating a first reported event associated with a first point or interval in time (e.g., 9 AM to 10 AM) and data indicating a second reported event associated with a second point or interval in time (e.g., 11 AM to 3 PM).

In some implementations, the events data acquisition operation 302 may include an operation 456 for acquiring data indicating incidence of a third one or more reported events as depicted in FIG. 4i. For instance, the events data acquisition module 102 of the computing device 10 acquiring data indicating incidence of a third one or more reported events. For example, acquiring a third one or more reported events that may not be associated with or be relevant (e.g., "noise" data) to the hypothesis to be developed.

Figure 5:
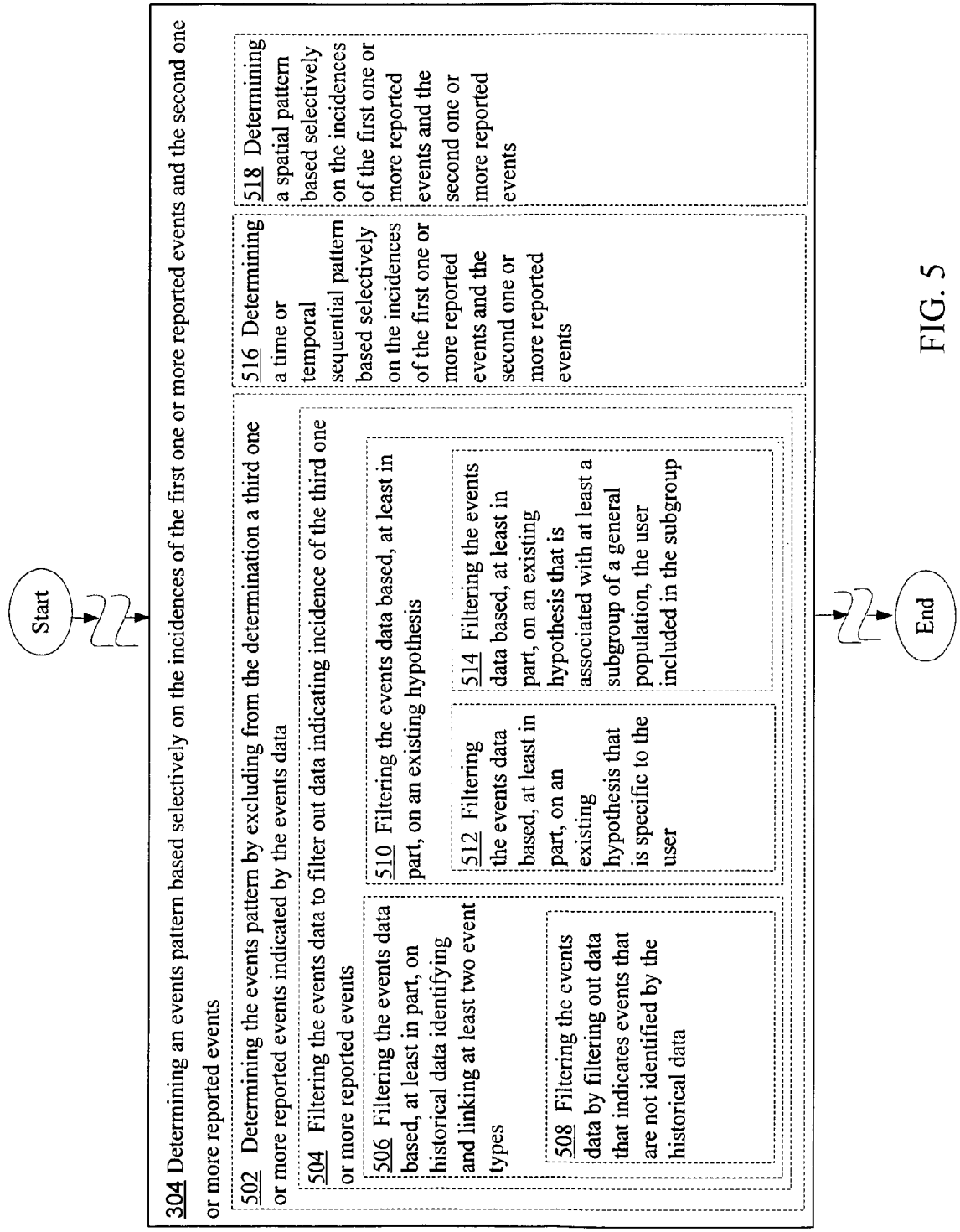
FIG. 5 is a high-level logic flowchart of a process depicting alternate implementations of the events pattern determination operation 304 of FIG. 3.

Referring back to FIG. 3, the events pattern determination operation 304 in various implementations may be performed in a number of different ways. For example, in some implementations, the events pattern determination operation 304 may include an operation 502 for determining the events pattern by excluding from the determination a third one or more reported events indicated by the events data as depicted in FIG. 5. For instance, the events pattern determination module 104 of the computing device 10 determining the events pattern by the exclusion module 208 (see FIG. 2b) excluding from the determination a third one or more reported events indicated by the events data 60*.

In various implementations, operation 502 may include an operation 504 for filtering the events data to filter out data indicating incidence of the third one or more reported events as depicted in FIG. 5. For instance, the filter module 210 (see FIG. 2b) of the computing device 10 filtering the events data 60* to filter out data indicating incidence of the third one or more reported events 63*.

Operation 504, in turn, may include one or more additional operations in various alternative implementations. For example, in some implementations, operation 504 may include an operation 506 for filtering the events data based, at least in part, on historical data identifying and linking at least two event types as depicted in FIG. 5. For instance, the filter module 210 of the computing device 10 filtering the events data 60* based, at least in part, on the historical data referencing module 212 (see FIG. 2b) referencing historical data 82 identifying and linking at least two event types (e.g., excessive consumption of food and upset stomach).

Operation 506, in various implementations, may further include an operation 508 for filtering the events data by filtering out data that indicates events that are not identified by the historical data as depicted in FIG. 5. For instance, the filter module 210 of the computing device 10 filtering the events data 60* by filtering out data that indicates events that are not identified by the historical data 82.

In some implementations, operation 504 may include an operation 510 for filtering the events data based, at least in part, on an existing hypothesis as depicted in FIG. 5. For instance, the filter module 210 of the computing device 10 filtering the events data 60* based, at least in part, on an existing hypothesis 80 referenced by the hypothesis referencing module 214.

Operation 510, in turn, may include one or more additional operations in various alternative implementations. For example, in some implementations, operation 510 may include an operation 512 for filtering the events data based, at least in part, on an existing hypothesis that is specific to the user as depicted in FIG. 5. For instance, the filter module 210 of the computing device 10 filtering the events data 60* based, at least in part, the hypothesis referencing module 214 referencing on an existing hypothesis 80 that is specific to the user 20*. For example, such an existing hypothesis 80 may have been initially created based on events data 60* that was specifically associated with the user 20*.

In some implementations, operation 510 may include an operation 514 for filtering the events data based, at least in part, on an existing hypothesis that is associated with at least a subgroup of a general population, the user included in the subgroup as depicted in FIG. 5. For instance, the filter module 210 of the computing device 10 filtering the events data 60* based, at least in part, on the hypothesis referencing module 214 referencing an existing hypothesis 80 that is associated with at least a subgroup of a general population, the user 20* included in the subgroup. For example, such an existing hypothesis 80 may be specifically related to a particular ethnic group.

Referring back to the events pattern determination operation 304 of FIG. 3, in some implementations, the events pattern determination operation 304 may include an operation 516 for determining a time or temporal sequential pattern based selectively on the incidences of the first one or more reported events and the second one or more reported events as depicted in FIG. 5. For instance, the events pattern determination module 104 of the computing device 10 determining a time or temporal sequential pattern based selectively on the incidences of the first one or more reported events and the second one or more reported events. The determination of the sequential pattern may involve the determination of the time or temporal relationship between at least a first event type (e.g., a subjective user state such as a hangover) and a second event type (e.g., an objective occurrence such as consumption of an alcoholic beverage).

In some implementations, the events pattern determination operation 304 may include an operation 518 for determining a spatial pattern based selectively on the incidences of the first one or more reported events and the second one or more reported events as depicted in FIG. 5. For instance, the events pattern determination module 104 of the computing device 10 determining a spatial pattern based selectively on the incidences of the first one or more reported events and the second one or more reported events. The determination of the spatial pattern may involve the determination of spatial relationships between at least a first event type (e.g., a subjective user state such as feeling happy at work) and a second event type (e.g., an objective occurrence such as the boss being away on vacation in Hawaii).

Figure 6A:
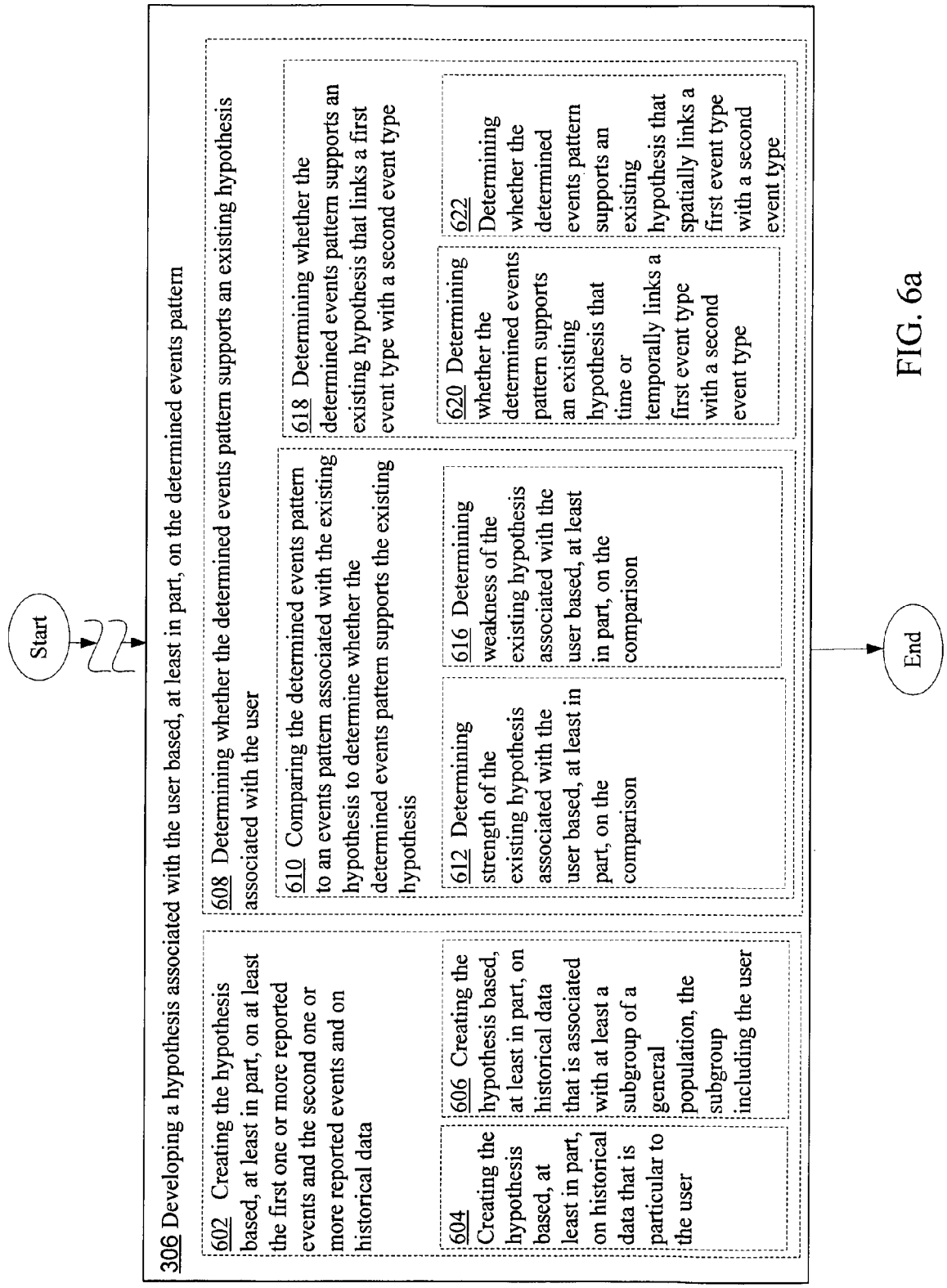
FIG. 6a is a high-level logic flowchart of a process depicting alternate implementations of the hypothesis development operation 306 of FIG. 3.

Referring back to the hypothesis development operation 306 of FIG. 3, in various implementations, the hypothesis development operation 306 may be executed in a number of different ways depending upon, for example, whether a hypothesis is being created or an existing hypothesis 80 is being further developed or revised. For example, in some implementations, the hypothesis development operation 306 may include a creation operation 602 for creating the hypothesis based, at least in part, on at least the first one or more reported events and the second one or more reported events and on historical data as depicted in FIG. 6a. For instance, the hypothesis creation module 216 (see FIG. 2c) of the computing device 10 creating the hypothesis based, at least in part, on at least the first one or more reported events and the second one or more reported events (e.g., as indicated by the event data 60*) and on historical data 82 (e.g., historical sequential or spatial events patterns associated with at least the user 20*) as referenced by, for example, the historical data referencing module 220.

In some implementations, the creation operation 602 may include an operation 604 for creating the hypothesis based, at least in part, on historical data that is particular to the user as depicted in FIG. 6a. For instance, the hypothesis creation module 216 of the computing device 10 creating the hypothesis based, at least in part, on historical data 82 (e.g., as referenced by the historical data referencing module 220) that is particular to the user 20*.

In some implementations, the creation operation 602 may include an operation 606 for creating the hypothesis based, at least in part, on historical data that is associated with at least a subgroup of a general population, the subgroup including the user as depicted in FIG. 6a. For instance, the hypothesis creation module 216 of the computing device 10 creating the hypothesis based, at least in part, on historical data 82 (e.g., as referenced by the historical data referencing module 220) that is associated with at least a subgroup of a general population, the subgroup including the user 20*.

The hypothesis development operation 306 of FIG. 3, in various implementations, may comprise one or more operations for updating or further developing of an existing hypothesis 80. For example, in some implementations, the hypothesis development operation 306 may include a determination operation 608 for determining whether the determined events pattern supports an existing hypothesis associated with the user as depicted in FIG. 6a. For instance, the determination module 222 (see FIG. 2c) of the computing device 10 determining whether an events pattern (e.g., as determined by the events pattern determination module 104) supports an existing hypothesis 80 associated with the user 20*.

In various implementations, the determination operation 608 may be executed in a number of different ways depending upon circumstances. For example, in various implementations, the determination operation 608 may include a comparison operation 610 for comparing the determined events pattern to an events pattern associated with the existing hypothesis to determine whether the determined events pattern supports the existing hypothesis as depicted in FIG. 6a. For instance, the comparison module 224 (e.g., see FIG. 2c) of the computing device 10 comparing the determined events pattern (e.g., as determined by the events pattern determination module 104) to an events pattern associated with the existing hypothesis 80 to determine whether the determined events pattern supports the existing hypothesis 80.

In some implementations, the comparison operation 610 may include an operation 612 for determining strength of the existing hypothesis associated with the user based, at least in part, on the comparison as depicted in FIG. 6a. For instance, the strength determination module 226 of the computing device 10 determining the strength of the existing hypothesis 80 associated with the user 20* based, at least in part, on the comparison. That is, by determining how similar the determined events pattern is to the events pattern associated with the existing hypothesis 80, a determination may be made as to the strength of the existing hypothesis 80. For example, suppose the existing hypothesis 80 relates to an alleged association or link between two event types. If the determined events pattern is similar or matches the events pattern associated with the existing hypothesis 80, then this may indicate a strong or stronger link between the two event types.

In some implementations, the comparison operation 610 may include an operation 616 for determining weakness of the existing hypothesis associated with the user based, at least in part, on the comparison as depicted in FIG. 6a. For instance, the weakness determination module 228 of the computing device 10 determining the weakness of the existing hypothesis 80 associated with the user 20* based, at least in part, on the comparison. That is, by determining how different the determined events pattern is to the events pattern associated with the existing hypothesis 80, a determination may be made as to the weakness of the existing hypothesis 80. For example, suppose the existing hypothesis 80 relates to an alleged association or link between two event types. If the determined events pattern is determined to be dissimilar to the events pattern associated with the existing hypothesis 80, then this may indicate a weak or weaker link between the two event types.

In various implementations, the determination operation 608 may include an operation 618 for determining whether the determined events pattern supports an existing hypothesis that links a first event type with a second event type as depicted in FIG. 6a. For instance, the determination module 222 of the computing device 10 determining whether the determined events pattern (e.g., as determined by the events pattern determination module 104 of FIG. 2b and referenced by the determined events pattern referencing module 230 of FIG. 2c) supports an existing hypothesis 80 that links a first event type (e.g., a subjective mental state such as drowsiness) with a second event type (e.g., consumption of a medicine such as cold medication).

In some implementations, operation 618 may include an operation 620 for determining whether the determined events pattern supports an existing hypothesis that time or temporally links a first event type with a second event type as depicted in FIG. 6a. For instance, the determination module 222 of the computing device 10 determining whether the determined events pattern (e.g., as determined by the events pattern determination module 104 and referenced by the determined events pattern referencing module 230) supports an existing hypothesis 80 that sequentially (e.g., time or temporally) links a first event type (e.g., a hangover) with a second event type (e.g., binge drinking).

In some implementations, operation 618 may include an operation 622 for determining whether the determined events pattern supports an existing hypothesis that spatially links a first event type with a second event type as depicted in FIG. 6a. For instance, the determination module 222 of the computing device 10 determining whether the determined events pattern (e.g., as determined by the events pattern determination module 104 and referenced by the determined events pattern referencing module 230) supports an existing hypothesis 80 that spatially links a first event type (e.g., in-laws visiting home) with a second event type (e.g., feeling tension at home).

Figure 6B:
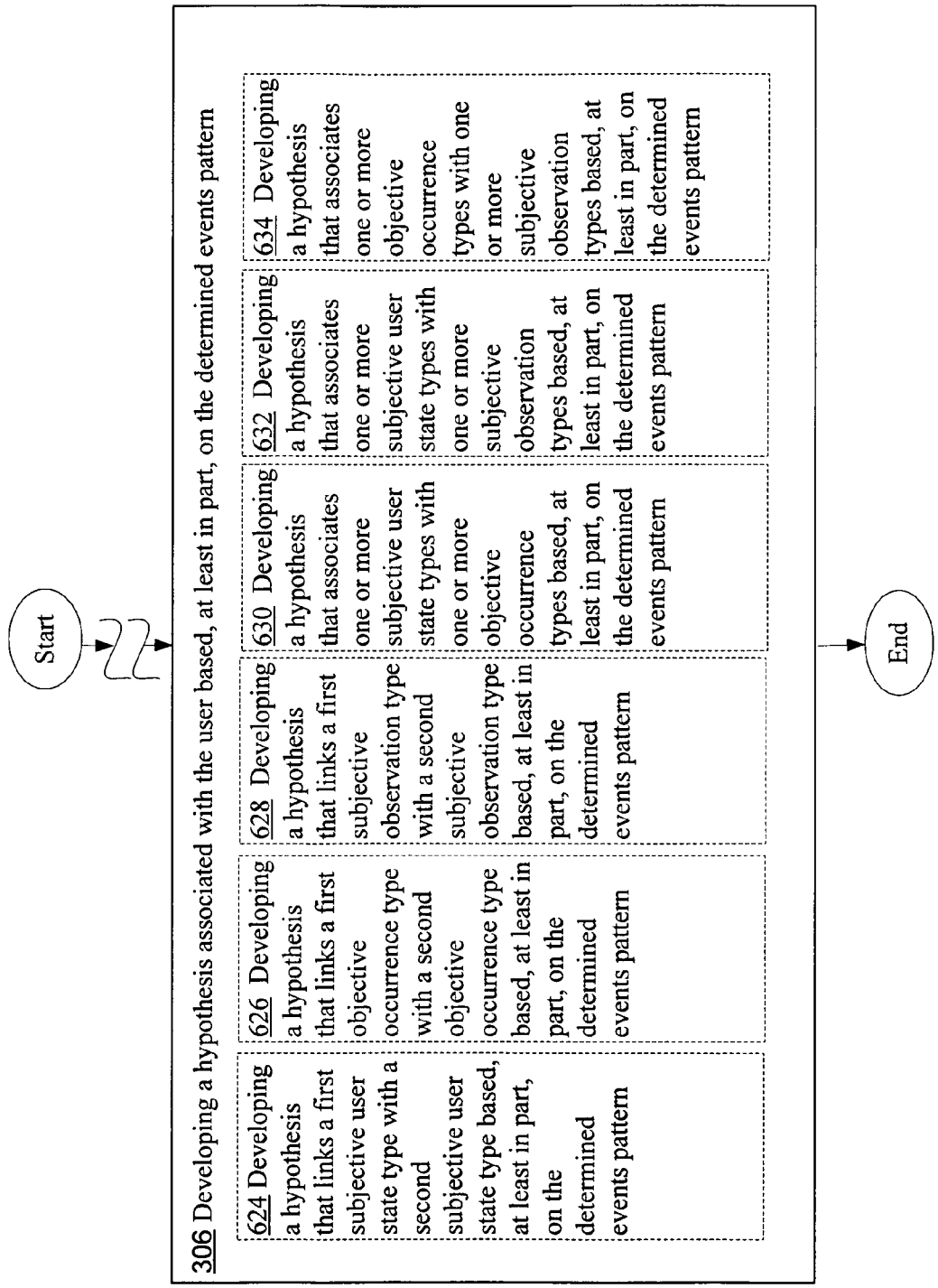
FIG. 6b is a high-level logic flowchart of a process depicting alternate implementations of the hypothesis development operation 306 of FIG. 3.

In various implementations, the hypothesis development operation 306 of FIG. 3 may include an operation 624 for developing a hypothesis that links a first subjective user state type with a second subjective user state type based, at least in part, on the determined events pattern as depicted in FIG. 6b. For instance, the hypothesis development module 106 of the computing device 10 developing a hypothesis that links a first subjective user state type (e.g., tension) with a second subjective user state type (e.g., upset stomach) based, at least in part, on the determined events pattern (e.g., as determined by the events pattern determination module 104 and referenced by the determined events pattern referencing module 230).

In some implementations, the hypothesis development operation 306 may include an operation 626 for developing a hypothesis that links a first objective occurrence type with a second objective occurrence type based, at least in part, on the determined events pattern as depicted in FIG. 6b. For instance, the hypothesis development module 106 of the computing device 10 developing a hypothesis that links a first objective occurrence type (e.g., consuming a particular type of food item) with a second objective occurrence type (e.g., increased bowel movement) based, at least in part, on the determined events pattern (e.g., as determined by the events pattern determination module 104 and referenced by the determined events pattern referencing module 230).

In some implementations, the hypothesis development operation 306 may include an operation 628 for developing a hypothesis that links a first subjective observation type with a second subjective observation type based, at least in part, on the determined events pattern as depicted in FIG. 6b. For instance, the hypothesis development module 106 of the computing device 10 developing a hypothesis that links a first subjective observation type (e.g., good weather) with a second subjective observation type (e.g., sulking behavior) based, at least in part, on the determined events pattern (e.g., as determined by the events pattern determination module 104 and referenced by the determined events pattern referencing module 230).

In some implementations, the hypothesis development operation 306 may include an operation 630 for developing a hypothesis that associates one or more subjective user state types with one or more objective occurrence types based, at least in part, on the determined events pattern as depicted in FIG. 6b. For instance, the hypothesis development module 106 of the computing device 10 developing a hypothesis that associates one or more subjective user state types (e.g., happiness) with one or more objective occurrence types (e.g., spending time with children) based, at least in part, on the determined events pattern (e.g., as determined by the events pattern determination module 104 and referenced by the determined events pattern referencing module 230).

In some implementations, the hypothesis development operation 306 may include an operation 632 for developing a hypothesis that associates one or more subjective user state types with one or more subjective observation types based, at least in part, on the determined events pattern as depicted in FIG. 6b. For instance, the hypothesis development module 106 of the computing device 10 developing a hypothesis that associates one or more subjective user state types (e.g., depression) with one or more subjective observation types (e.g., sluggish appearance) based, at least in part, on the determined events pattern (e.g., as determined by the events pattern determination module 104 and referenced by the determined events pattern referencing module 230).

In some implementations, the hypothesis development operation 306 may include an operation 634 for developing a hypothesis that associates one or more objective occurrence types with one or more subjective observation types based, at least in part, on the determined events pattern as depicted in FIG. 6b. For instance, the hypothesis development module 106 of the computing device 10 developing a hypothesis that associates one or more objective occurrence types (e.g., high blood pressure) with one or more subjective observation types (e.g., intense appearance) based, at least in part, on the determined events pattern (e.g., as determined by the events pattern determination module 104 and referenced by the determined events pattern referencing module 230).

Figure 7:
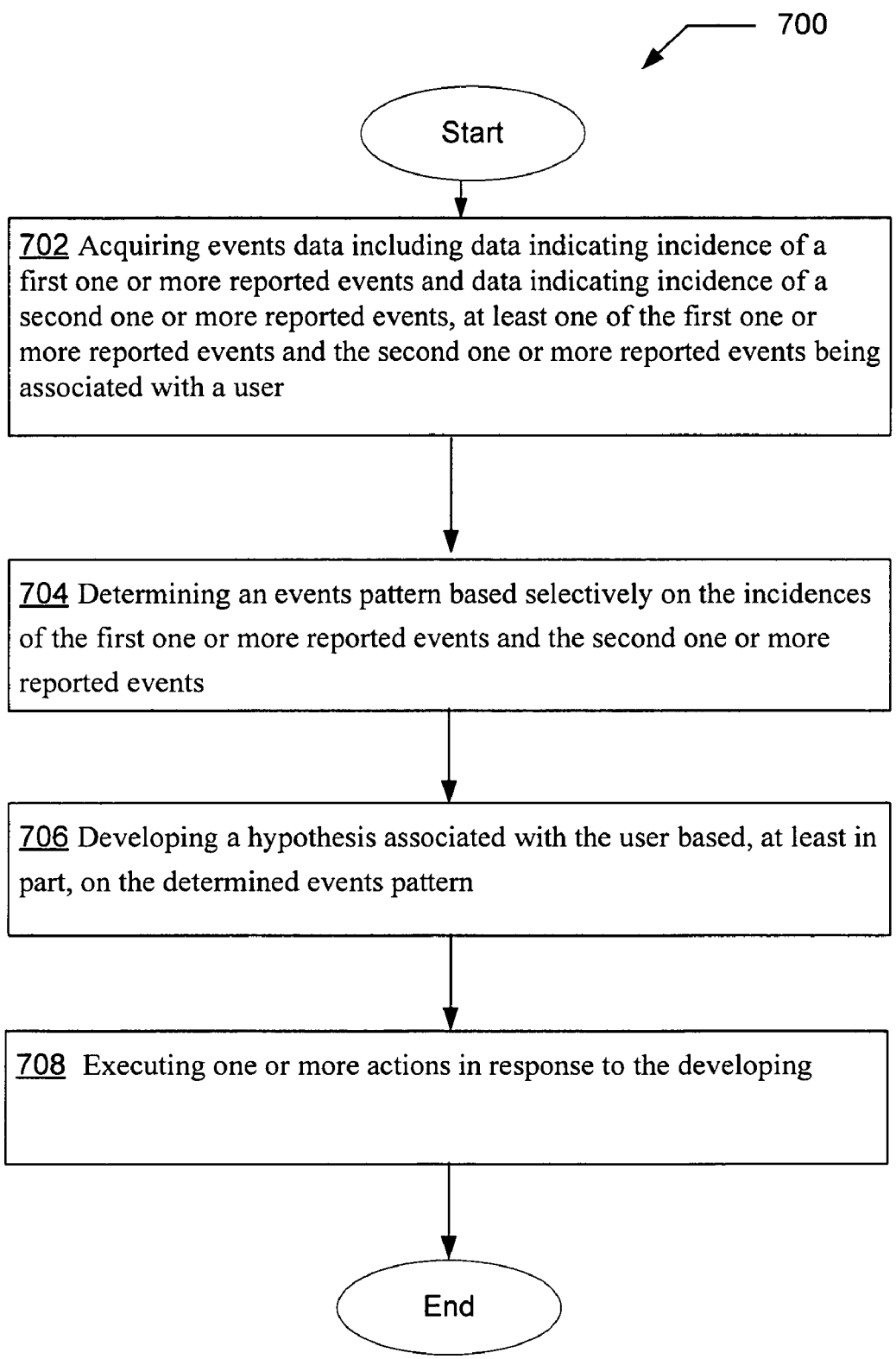
FIG. 7 is a high-level logic flowchart of another process.

Referring now to FIG. 7 illustrating another operational flow 700 in accordance with various embodiments. In some embodiments, operational flow 700 may be particularly suited to be performed by the computing device 10, which may be a network server or a standalone computing device. Operational flow 700 includes operations that mirror the operations included in the operational flow 300 of FIG. 3. For example, operational flow 700 may include an events data acquisition operation 702, an events pattern determination operation 704, and a hypothesis development operation 706 that corresponds to and mirror the events data acquisition operation 302, the events pattern determination operation 304, and the hypothesis development operation 706, respectively, of FIG. 3.

In addition, and unlike operational flow 300, operational flow 700 may further include an action execution operation 708 for executing one or more actions in response to the developing as depicted in FIG. 7. For instance, the action execution module 108 of the computing device 10 executing one or more actions (e.g., presenting results of the hypothesis development, initiating monitoring operations for particular event types, and so forth) in response to a hypothesis development operation 706 performed by, for example, the hypothesis development module 106.

Figure 8A:
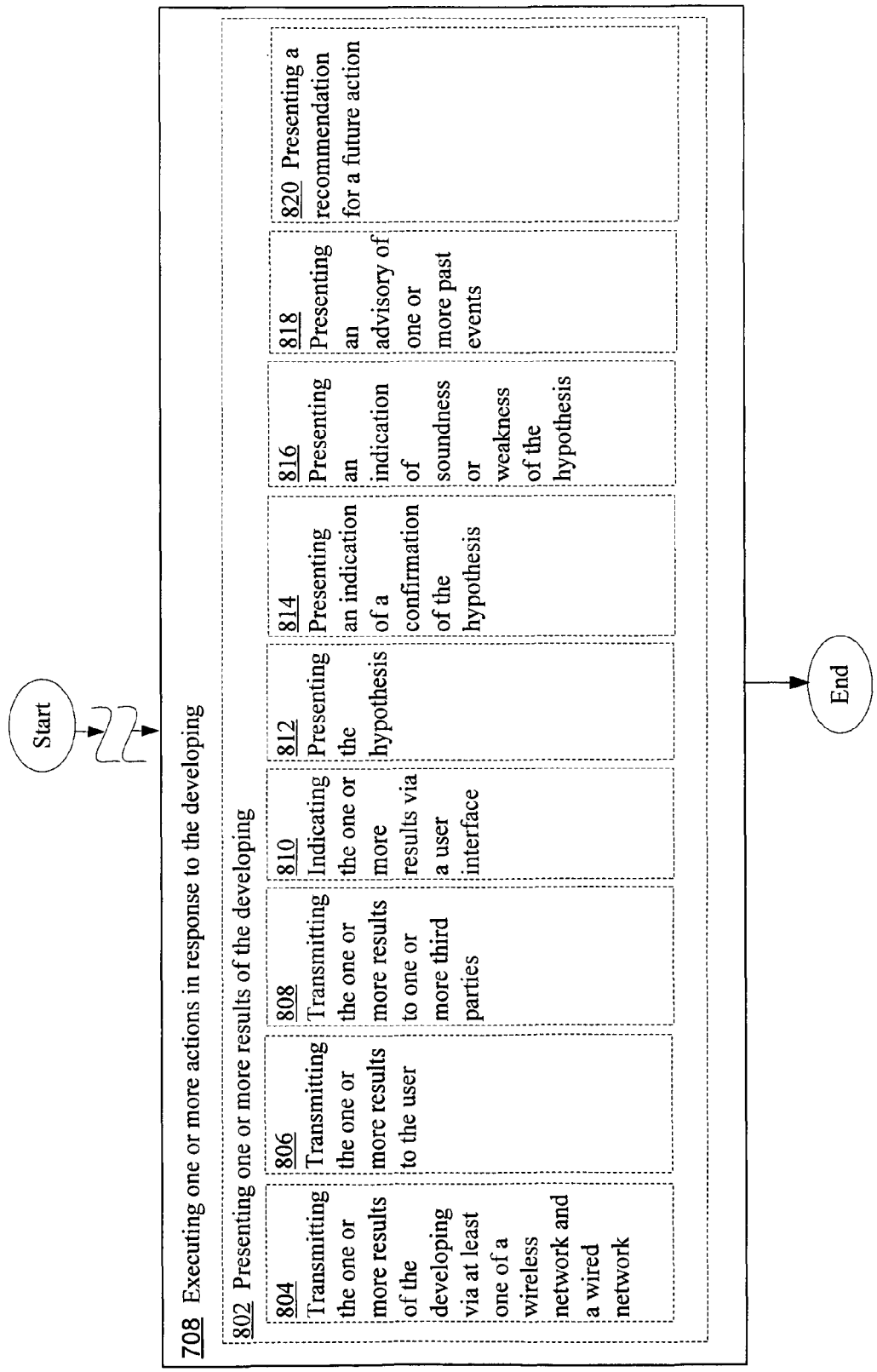
FIG. 8a is a high-level logic flowchart of a process depicting alternate implementations of the action execution operation 708 of FIG. 7.

In various implementations, the action execution operation 708 may be performed in a number of different ways depending upon the particular circumstances. For example, in some implementations, the action execution operation 708 may include a presentation operation 802 for presenting one or more results of the developing as depicted in FIG. 8a. For instance, the presentation module 232 (see FIG. 2d) of the computing device 10 presenting (e.g., transmitting via a network interface 120 or indicating via a user interface 122) one or more results 90 (e.g., an advisory related to the hypothesis) of the developing of the hypothesis as performed in the hypothesis development operation 706.

In various implementations, the presentation operation 802 may include one or more additional operations. For example, in some implementations, the presentation operation 802 may include an operation 804 for transmitting the one or more results of the developing via at least one of a wireless network and a wired network as depicted in FIG. 8a. For instance, the transmission module 234 of the computing device 10 transmitting (e.g., via network interface 120) the one or more results of the developing via a wireless and/or a wired network 40.

In some implementations, the presentation operation 802 may include an operation 806 for transmitting the one or more results to the user as depicted in FIG. 8a. For instance, the transmission module 234 of the computing device 10 transmitting the one or more results 90 to the user 20a.

In some implementations, the presentation operation 802 may include an operation 808 for transmitting the one or more results to one or more third parties as depicted in FIG. 8a. For instance, the transmission module 234 of the computing device 10 transmitting the one or more results 90 to one or more third parties (e.g., one or more third party sources 50).

In some implementations, the presentation operation 802 may include an operation 810 for indicating the one or more results via a user interface as depicted in FIG. 8a. For instance, the indication module 236 of the computing device 10 indicating the one or more results 90 via a user interface 122 (e.g., a display monitor, a touchscreen, a speaker, and so forth).

In some implementations, the presentation operation 802 may include an operation 812 for presenting the hypothesis as depicted in FIG. 8a. For instance, the hypothesis presentation module 238 of the computing device 10 presenting (e.g., transmitting or indicating) the hypothesis.

In some implementations, the presentation operation 802 may include an operation 814 for presenting an indication of a confirmation of the hypothesis as depicted in FIG. 8a. For instance, the hypothesis confirmation presentation module 240 of the computing device 10 presenting (e.g., via a network interface 120 or via a user interface 122) an indication of a confirmation of the hypothesis.

In some implementations, the presentation operation 802 may include an operation 816 for presenting an indication of soundness or weakness of the hypothesis as depicted in FIG. 8a. For instance, the hypothesis soundness/weakness presentation module 242 of the computing device 10 presenting (e.g., via a network interface 120 or via a user interface 122) an indication of soundness or weakness of the hypothesis.

In some implementations, the presentation operation 802 may include an operation 818 for presenting an advisory of one or more past events as depicted in FIG. 8a. For instance, the advisory presentation module 244 of the computing device 10 presenting an advisory (e.g., notification regarding a pattern of reported events such as "did you know that the last time you drank four mugs of beer, you had a hangover the next day").

In some implementations, the presentation operation 802 may include an operation 820 for presenting a recommendation for a future action as depicted in FIG. 8a. For instance, the recommendation presentation module 246 of the computing device 10 presenting a recommendation for a future action (e.g., "since you drank four mugs of beer last night, you should take two tablets of aspirin before you go to work in the morning").

Figure 8B:
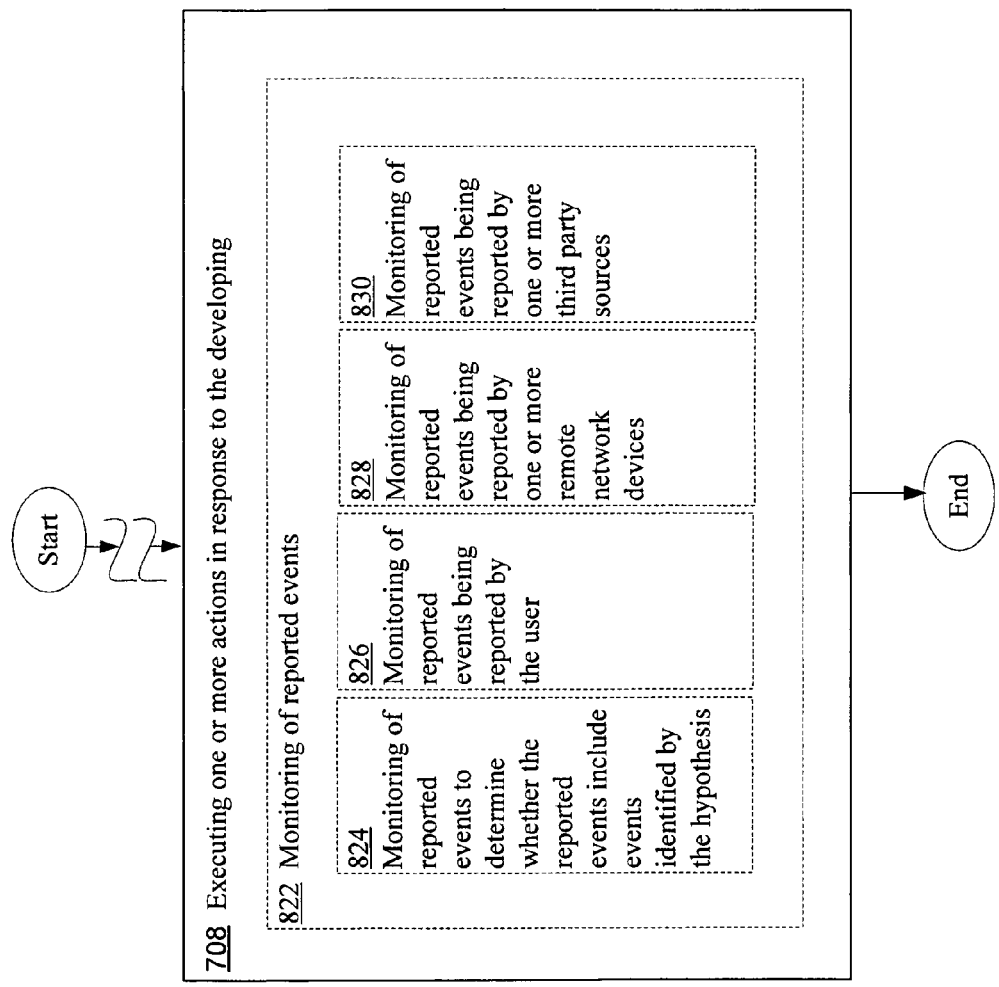
FIG. 8b is a high-level logic flowchart of a process depicting alternate implementations of the action execution operation 708 of FIG. 7.

In various implementations, the action execution operation 708 of FIG. 7 may include a monitoring operation 822 for monitoring of reported events as depicted in FIG. 8b. For instance, the monitoring module 250 of the computing device 10 monitoring of reported events (e.g., as reported by the user 20*, by one or more third party sources 50, or by one or more remote network devices such as sensors 35 or network servers 36).

In some implementations, the monitoring operation 822 may include an operation 824 for monitoring of reported events to determine whether the reported events include events identified by the hypothesis as depicted in FIG. 8b. For instance, the monitoring module 250 of the computing device 10 monitoring of reported events (e.g., reported via one or more blog entries, one or more status reports, one or more electronic messages, and so forth) to determine whether the reported events include events identified by the hypothesis.

In some implementations, the monitoring operation 822 may include an operation 826 for monitoring of reported events being reported by the user as depicted in FIG. 8b. For instance, the monitoring module 250 of the computing device 10 monitoring of reported events (e.g., reported via one or more blog entries, one or more status reports, one or more electronic messages, and so forth) being reported by the user 20*.

In some implementations, the monitoring operation 822 may include an operation 828 for monitoring of reported events being reported by one or more remote network devices as depicted in FIG. 8b. For instance, the monitoring module 250 of the computing device 10 monitoring of reported events (e.g., events reported via wireless and/or wired network 40) being reported by one or more remote network devices (e.g., sensors 35 and/or network servers 36).

In some implementations, the monitoring operation 822 may include an operation 830 for monitoring of reported events being reported by one or more third party sources as depicted in FIG. 8b. For instance, the monitoring module 250 of the computing device 10 monitoring of reported events (e.g., events reported via wireless and/or wired network 40) being reported by one or more third party sources 50.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented system in the form of a machine, article of manufacture, or composition of matter, comprising:
    means for acquiring events data including data indicating incidence of a first one or more reported events and data indicating incidence of a second one or more reported events, at least one of the first one or more reported events and the second one or more reported events being associated with a user, wherein said means for acquiring events data including data indicating incidence of a first one or more reported events and data indicating incidence of a second one or more reported events, at least one of the first one or more reported events and the second one or more reported events being associated with a user comprises:
        means for receiving at least one of the data indicating incidence of a first one or more reported events and the data indicating incidence of a second one or more reported events;
    means for determining an events pattern based selectively on the incidences of the first one or more reported events and the second one or more reported events; and
    means for developing a hypothesis associated with the user based, at least in part, on the determined events pattern.

2. The computationally-implemented system of claim 1, wherein said means for receiving at least one of the data indicating incidence of a first one or more reported events and the data indicating incidence of a second one or more reported events comprises:
    means for receiving at least one of the data indicating incidence of a first one or more reported events and the data indicating incidence of a second one or more reported events via one or more blog entries.

3. The computationally-implemented system of claim 1, wherein said means for receiving at least one of the data indicating incidence of a first one or more reported events and the data indicating incidence of a second one or more reported events comprises:
    means for receiving at least one of the data indicating incidence of a first one or more reported events and the data indicating incidence of a second one or more reported events via one or more status reports.

4. The computationally-implemented system of claim 1, wherein said means for receiving at least one of the data indicating incidence of a first one or more reported events and the data indicating incidence of a second one or more reported events comprises:
    means for receiving at least one of the data indicating incidence of a first one or more reported events and the data indicating incidence of a second one or more reported events via one or more electronic messages.

5. The computationally-implemented system of claim 1, wherein said means for determining an events pattern based selectively on the incidences of the first one or more reported events and the second one or more reported events comprises:
    means for determining the events pattern by excluding from the determination a third one or more reported events indicated by the events data.

6. The computationally-implemented system of claim 5, wherein said means for determining the events pattern by excluding from the determination a third one or more reported events indicated by the events data comprises:
    means for filtering the events data to filter out data indicating incidence of the third one or more reported events.

7. The computationally-implemented system of claim 6, wherein said means for filtering the events data to filter out data indicating incidence of the third one or more reported events comprises:
    means for filtering the events data based, at least in part, on historical data identifying and linking at least two event types.

8. The computationally-implemented system of claim 7, wherein said means for filtering the events data based, at least in part, on historical data identifying and linking at least two event types comprises:
    means for filtering the events data by filtering out data that indicates events that are not identified by the historical data.

9. The computationally-implemented system of claim 6, wherein said means for filtering the events data to filter out data indicating incidence of the third one or more reported events comprises:
    means for filtering the events data based, at least in part, on an existing hypothesis.

10. The computationally-implemented system of claim 9, wherein said means for filtering the events data based, at least in part, on an existing hypothesis comprises:
    means for filtering the events data based, at least in part, on an existing hypothesis that is specific to the user.

11. The computationally-implemented system of claim 9, wherein said means for filtering the events data based, at least in part, on an existing hypothesis comprises:
  means for filtering the events data based, at least in part, on an existing hypothesis that is associated with at least a subgroup of a general population, the user included in the subgroup.

12. The computationally-implemented system of claim 1, wherein said means for determining an events pattern based selectively on the incidences of the first one or more reported events and the second one or more reported events comprises:
  means for determining a time or temporal sequential pattern based selectively on the incidences of the first one or more reported events and the second one or more reported events.

13. The computationally-implemented system of claim 1, wherein said means for determining an events pattern based selectively on the incidences of the first one or more reported events and the second one or more reported events comprises:
  means for determining a spatial pattern based selectively on the incidences of the first one or more reported events and the second one or more reported events.

14. The computationally-implemented system of claim 1, wherein said means for developing a hypothesis associated with the user based, at least in part, on the determined events pattern comprises:
  means for creating the hypothesis based, at least in part, on at least the first one or more reported events and the second one or more reported events and on historical data.

15. The computationally-implemented system of claim 14, wherein said means for creating the hypothesis based, at least in part, on at least the first one or more reported events and the second one or more reported events and on historical data comprises:
  means for creating the hypothesis based, at least in part, on historical data that is particular to the user.

16. The computationally-implemented system of claim 14, wherein said means for creating the hypothesis based, at least in part, on at least the first one or more reported events and the second one or more reported events and on historical data comprises:
  means for creating the hypothesis based, at least in part, on historical data that is associated with at least a subgroup of a general population, the subgroup including the user.

17. The computationally-implemented system of claim 1, wherein said means for developing a hypothesis associated with the user based, at least in part, on the determined events pattern comprises:
  means for determining whether the determined events pattern supports an existing hypothesis associated with the user.

18. The computationally-implemented system of claim 17, wherein said means for determining whether the determined events pattern supports an existing hypothesis associated with the user comprises:
  means for comparing the determined events pattern to an events pattern associated with the existing hypothesis to determine whether the determined events pattern supports the existing hypothesis.

19. The computationally-implemented system of claim 18, wherein said means for comparing the determined events pattern to an events pattern associated with the existing hypothesis to determine whether the determined events pattern supports the existing hypothesis comprises:
  means for determining strength of the existing hypothesis associated with the user based, at least in part, on the comparison.

20. The computationally-implemented system of claim 17, wherein said means for determining whether the determined events pattern supports an existing hypothesis associated with the user comprises:
  means for determining whether the determined events pattern supports an existing hypothesis that links a first event type with a second event type.

21. The computationally-implemented system of claim 20, wherein said means for determining whether the determined events pattern supports an existing hypothesis that links a first event type with a second event type comprises:
  means for determining whether the determined events pattern supports an existing hypothesis that time or temporally links a first event type with a second event type.

22. The computationally-implemented system of claim 20, wherein said means for determining whether the determined events pattern supports an existing hypothesis that links a first event type with a second event type comprises:
  means for determining whether the determined events pattern supports an existing hypothesis that spatially links a first event type with a second event type.

23. The computationally-implemented system of claim 1, wherein said means for developing a hypothesis associated with the user based, at least in part, on the determined events pattern comprises:
  means for developing a hypothesis that links a first subjective user state type with a second subjective user state type based, at least in part, on the determined events pattern.

24. The computationally-implemented system of claim 1, wherein said means for developing a hypothesis associated with the user based, at least in part, on the determined events pattern comprises:
  means for developing a hypothesis that links a first objective occurrence type with a second objective occurrence type based, at least in part, on the determined events pattern.

25. The computationally-implemented system of claim 1, wherein said means for developing a hypothesis associated with the user based, at least in part, on the determined events pattern comprises:
  means for developing a hypothesis that links a first subjective observation type with a second subjective observation type based, at least in part, on the determined events pattern.

26. The computationally-implemented system of claim 1, wherein said means for developing a hypothesis associated with the user based, at least in part, on the determined events pattern comprises:
  means for developing a hypothesis that associates one or more subjective user state types with one or more objective occurrence types based, at least in part, on the determined events pattern.

27. The computationally-implemented system of claim 1, wherein said means for developing a hypothesis associated with the user based, at least in part, on the determined events pattern comprises:
  means for developing a hypothesis that associates one or more subjective user state types with one or more subjective observation types based, at least in part, on the determined events pattern.

28. The computationally-implemented system of claim 1, wherein said means for developing a hypothesis associated with the user based, at least in part, on the determined events pattern comprises:
    means for developing a hypothesis that associates one or more objective occurrence types with one or more subjective observation types based, at least in part, on the determined events pattern.

29. The computationally-implemented system of claim 1, further comprising:
    means for executing one or more actions in response to the developing.

30. The computationally-implemented system of claim 29, wherein said means for executing one or more actions in response to the developing comprises:
    means for presenting one or more results of the developing.

31. The computationally-implemented system of claim 30, wherein said means for presenting one or more results of the developing comprises:
    means for presenting the hypothesis.

32. The computationally-implemented system of claim 30, wherein said means for presenting one or more results of the developing comprises:
    means for presenting an indication of a confirmation of the hypothesis.

33. The computationally-implemented system of claim 30, wherein said means for presenting one or more results of the developing comprises:
    means for presenting an indication of soundness or weakness of the hypothesis.

34. The computationally-implemented system of claim 30, wherein said means for presenting one or more results of the developing comprises:
    means for presenting an advisory of one or more past events.

35. The computationally-implemented system of claim 30, wherein said means for presenting one or more results of the developing comprises:
    means for presenting a recommendation for a future action.

36. The computationally-implemented system of claim 29, wherein said means for executing one or more actions in response to the developing comprises:
    means for monitoring of reported events.

37. The computationally-implemented system of claim 36, wherein said means for monitoring of reported events comprises:
    means for monitoring of reported events to determine whether the reported events include events identified by the hypothesis.

38. The computationally-implemented system of claim 36, wherein said means for monitoring of reported events comprises:
    means for monitoring of reported events being reported by the user.

39. The computationally-implemented system of claim 36, wherein said means for monitoring of reported events comprises:
    means for monitoring of reported events being reported by one or more remote network devices.

40. The computationally-implemented system of claim 36, wherein said means for monitoring of reported events comprises:
    means for monitoring of reported events being reported by one or more third party sources.

41. A computationally-implemented system in the form of a machine, article of manufacture, or composition of matter, comprising:
    means for acquiring events data including data indicating incidence of a first one or more reported events and data indicating incidence of a second one or more reported events, at least one of the first one or more reported events and the second one or more reported events being associated with a user;
    means for determining an events pattern based selectively on the incidences of the first one or more reported events and the second one or more reported events, wherein said means for determining an events pattern based selectively on the incidences of the first one or more reported events and the second one or more reported events comprises:
        means for determining the events pattern by excluding from the determination a third one or more reported events indicated by the events data; and
    means for developing a hypothesis associated with the user based, at least in part, on the determined events pattern.

42. The computationally-implemented system of claim 41, wherein said means for determining the events pattern by excluding from the determination a third one or more reported events indicated by the events data comprises:
    means for filtering the events data to filter out data indicating incidence of the third one or more reported events.

43. The computationally-implemented system of claim 42, wherein said means for filtering the events data to filter out data indicating incidence of the third one or more reported events comprises:
    means for filtering the events data based, at least in part, on an existing hypothesis.

44. The computationally-implemented system of claim 43, wherein said means for filtering the events data based, at least in part, on an existing hypothesis comprises:
    means for filtering the events data based, at least in part, on an existing hypothesis that is specific to the user.

45. The computationally-implemented system of claim 43, wherein said means for filtering the events data based, at least in part, on an existing hypothesis comprises:
    means for filtering the events data based, at least in part, on an existing hypothesis that is associated with at least a subgroup of a general population, the user included in the subgroup.

46. A computationally-implemented system in the form of a machine, article of manufacture, or composition of matter, comprising:
    means for acquiring events data including data indicating incidence of a first one or more reported events and data indicating incidence of a second one or more reported events, at least one of the first one or more reported events and the second one or more reported events being associated with a user;
    means for determining an events pattern based selectively on the incidences of the first one or more reported events and the second one or more reported events, wherein said means for determining an events pattern based selectively on the incidences of the first one or more reported events and the second one or more reported events comprises:
        means for determining a time or temporal sequential pattern based selectively on the incidences of the first one or more reported events and the second one or more reported events; and
    means for developing a hypothesis associated with the user based, at least in part, on the determined events pattern.

47. A computationally-implemented system in the form of a machine, article of manufacture, or composition of matter, comprising:

means for acquiring events data including data indicating incidence of a first one or more reported events and data indicating incidence of a second one or more reported events, at least one of the first one or more reported events and the second one or more reported events being associated with a user;

means for determining an events pattern based selectively on the incidences of the first one or more reported events and the second one or more reported events, wherein said means for determining an events pattern based selectively on the incidences of the first one or more reported events and the second one or more reported events comprises:

means for determining a spatial pattern based selectively on the incidences of the first one or more reported events and the second one or more reported events; and means for developing a hypothesis associated with the user based, at least in part, on the determined events pattern.

48. A computationally-implemented system in the form of a machine, article of manufacture, or composition of matter, comprising:

means for acquiring events data including data indicating incidence of a first one or more reported events and data indicating incidence of a second one or more reported events, at least one of the first one or more reported events and the second one or more reported events being associated with a user;

means for determining an events pattern based selectively on the incidences of the first one or more reported events and the second one or more reported events; and means for developing a hypothesis associated with the user based, at least in part, on the determined events pattern, wherein said means for developing a hypothesis associated with the user based, at least in part, on the determined events pattern comprises:

means for creating the hypothesis based, at least in part, on at least the first one or more reported events and the second one or more reported events and on historical data.

49. The computationally-implemented system of claim 48, wherein said means for creating the hypothesis based, at least in part, on at least the first one or more reported events and the second one or more reported events and on historical data comprises:

means for creating the hypothesis based, at least in part, on historical data that is particular to the user.

50. The computationally-implemented system of claim 48, wherein said means for creating the hypothesis based, at least in part, on at least the first one or more reported events and the second one or more reported events and on historical data comprises:

means for creating the hypothesis based, at least in part, on historical data that is associated with at least a subgroup of a general population, the subgroup including the user.

51. A computationally-implemented system in the form of a machine, article of manufacture, or composition of matter, comprising:

means for acquiring events data including data indicating incidence of a first one or more reported events and data indicating incidence of a second one or more reported events, at least one of the first one or more reported events and the second one or more reported events being associated with a user;

means for determining an events pattern based selectively on the incidences of the first one or more reported events and the second one or more reported events; and means for developing a hypothesis associated with the user based, at least in part, on the determined events pattern, wherein said means for developing a hypothesis associated with the user based, at least in part, on the determined events pattern comprises:

means for determining whether the determined events pattern supports an existing hypothesis associated with the user.

52. The computationally-implemented system of claim 51, wherein said means for determining whether the determined events pattern supports an existing hypothesis associated with the user comprises:

means for comparing the determined events pattern to an events pattern associated with the existing hypothesis to determine whether the determined events pattern supports the existing hypothesis.

53. The computationally-implemented system of claim 52, wherein said means for comparing the determined events pattern to an events pattern associated with the existing hypothesis to determine whether the determined events pattern supports the existing hypothesis comprises:

means for determining strength of the existing hypothesis associated with the user based, at least in part, on the comparison.

54. A computationally-implemented system in the form of a machine, article of manufacture, or composition of matter, comprising:

means for acquiring events data including data indicating incidence of a first one or more reported events and data indicating incidence of a second one or more reported events, at least one of the first one or more reported events and the second one or more reported events being associated with a user;

means for determining an events pattern based selectively on the incidences of the first one or more reported events and the second one or more reported events; and means for developing a hypothesis associated with the user based, at least in part, on the determined events pattern, wherein said means for developing a hypothesis associated with the user based, at least in part, on the determined events pattern comprises:

means for developing a hypothesis that links a first subjective user state type with a second subjective user state type based, at least in part, on the determined events pattern.

55. A computationally-implemented system in the form of a machine, article of manufacture, or composition of matter, comprising:

means for acquiring events data including data indicating incidence of a first one or more reported events and data indicating incidence of a second one or more reported events, at least one of the first one or more reported events and the second one or more reported events being associated with a user;

means for determining an events pattern based selectively on the incidences of the first one or more reported events and the second one or more reported events; and means for developing a hypothesis associated with the user based, at least in part, on the determined events pattern, wherein said means for developing a hypothesis associated with the user based, at least in part, on the determined events pattern comprises:

means for developing a hypothesis that links a first objective occurrence type with a second objective occurrence type based, at least in part, on the determined events pattern.

56. A computationally-implemented system in the form of a machine, article of manufacture, or composition of matter, comprising:
- means for acquiring events data including data indicating incidence of a first one or more reported events and data indicating incidence of a second one or more reported events, at least one of the first one or more reported events and the second one or more reported events being associated with a user;
- means for determining an events pattern based selectively on the incidences of the first one or more reported events and the second one or more reported events; and
- means for developing a hypothesis associated with the user based, at least in part, on the determined events pattern, wherein said means for developing a hypothesis associated with the user based, at least in part, on the determined events pattern comprises:
  - means for developing a hypothesis that links a first subjective observation type with a second subjective observation type based, at least in part, on the determined events pattern.

57. A computationally-implemented system in the form of a machine, article of manufacture, or composition of matter, comprising:
- means for acquiring events data including data indicating incidence of a first one or more reported events and data indicating incidence of a second one or more reported events, at least one of the first one or more reported events and the second one or more reported events being associated with a user;
- means for determining an events pattern based selectively on the incidences of the first one or more reported events and the second one or more reported events; and
- means for developing a hypothesis associated with the user based, at least in part, on the determined events pattern, wherein said means for developing a hypothesis associated with the user based, at least in part, on the determined events pattern comprises:
  - means for developing a hypothesis that associates one or more subjective user state types with one or more objective occurrence types based, at least in part, on the determined events pattern.

58. A computationally-implemented system in the form of a machine, article of manufacture, or composition of matter, comprising:
- means for acquiring events data including data indicating incidence of a first one or more reported events and data indicating incidence of a second one or more reported events, at least one of the first one or more reported events and the second one or more reported events being associated with a user;
- means for determining an events pattern based selectively on the incidences of the first one or more reported events and the second one or more reported events; and
- means for developing a hypothesis associated with the user based, at least in part, on the determined events pattern, wherein said means for developing a hypothesis associated with the user based, at least in part, on the determined events pattern comprises:
  - means for developing a hypothesis that associates one or more subjective user state types with one or more subjective observation types based, at least in part, on the determined events pattern.

59. A computationally-implemented system in the form of a machine, article of manufacture, or composition of matter, comprising:
- means for acquiring events data including data indicating incidence of a first one or more reported events and data indicating incidence of a second one or more reported events, at least one of the first one or more reported events and the second one or more reported events being associated with a user;
- means for determining an events pattern based selectively on the incidences of the first one or more reported events and the second one or more reported events; and
- means for developing a hypothesis associated with the user based, at least in part, on the determined events pattern, wherein said means for developing a hypothesis associated with the user based, at least in part, on the determined events pattern comprises:
  - means for developing a hypothesis that associates one or more objective occurrence types with one or more subjective observation types based, at least in part, on the determined events pattern.

60. A computationally-implemented system in the form of a machine, article of manufacture, or composition of matter, comprising:
- means for acquiring events data including data indicating incidence of a first one or more reported events and data indicating incidence of a second one or more reported events, at least one of the first one or more reported events and the second one or more reported events being associated with a user;
- means for determining an events pattern based selectively on the incidences of the first one or more reported events and the second one or more reported events; and
- means for developing a hypothesis associated with the user based, at least in part, on the determined events pattern; and
- means for executing one or more actions in response to the developing.

61. The computationally-implemented system of claim 60, wherein said means for executing one or more actions in response to the developing comprises:
- means for presenting one or more results of the developing.

62. The computationally-implemented system of claim 61, wherein said means for presenting one or more results of the developing comprises:
- means for presenting an indication of soundness or weakness of the hypothesis.

63. The computationally-implemented system of claim 60, wherein said means for executing one or more actions in response to the developing comprises:
- means for monitoring of reported events.

64. The computationally-implemented system of claim 63, wherein said means for monitoring of reported events comprises:
- means for monitoring of reported events to determine whether the reported events include events identified by the hypothesis.

* * * * *